United States Patent
Petry et al.

(10) Patent No.: US 9,029,400 B2
(45) Date of Patent: May 12, 2015

(54) 5-OXOISOXAZOLES AS INHIBITORS OF LIPASES AND PHOSPHOLIPASES

(75) Inventors: Stefan Petry, Frankfurt am Main (DE); Manfred Seidel, Frankfurt am Main (DE); Gerhard Zoller, Schöneck (DE); Gunter Müller, Frankfurt am Main (DE); Karl-Heinz Baringhaus, Frankfurt am Main (DE); Hubert Heuer, Frankfurt am Main (DE)

(73) Assignee: Sanofi, Paris (FR)

( * ) Notice: Subject to any disclaimer, the term of this patent is extended or adjusted under 35 U.S.C. 154(b) by 821 days.

(21) Appl. No.: 12/573,335

(22) Filed: Oct. 5, 2009

(65) Prior Publication Data

US 2010/0152246 A1     Jun. 17, 2010

Related U.S. Application Data

(63) Continuation of application No. PCT/EP2008/002314, filed on Mar. 22, 2008.

(30) Foreign Application Priority Data

Apr. 5, 2007 (EP) .................................. 07007251

(51) Int. Cl.
| | |
|---|---|
| A61K 31/4439 | (2006.01) |
| C07D 261/04 | (2006.01) |
| A61K 31/42 | (2006.01) |
| C07D 413/12 | (2006.01) |
| C07D 261/20 | (2006.01) |
| A61K 31/423 | (2006.01) |
| A61P 3/10 | (2006.01) |
| A61P 3/00 | (2006.01) |
| A61P 9/10 | (2006.01) |
| C07D 261/12 | (2006.01) |
| C07D 413/04 | (2006.01) |
| C07D 413/14 | (2006.01) |

(52) U.S. Cl.
CPC ............ *C07D 261/12* (2013.01); *C07D 261/20* (2013.01); *C07D 413/04* (2013.01); *C07D 413/12* (2013.01); *C07D 413/14* (2013.01)

(58) Field of Classification Search
None
See application file for complete search history.

(56) References Cited

FOREIGN PATENT DOCUMENTS

| | | |
|---|---|---|
| WO | WO 01/44211 | 6/2001 |
| WO | WO 2004/093872 A1 | 11/2004 |
| WO | WO 2004/094393 | 11/2004 |
| WO | WO 2004/094394 A1 | 11/2004 |
| WO | WO 2005/073199 | 8/2005 |
| WO | WO 2006/111321 | 10/2006 |

OTHER PUBLICATIONS

Lowe et al. in Journal of Bioorganic and Medicinal Chemistry Letters 14 (2004) 3155-3159.*
Remington's Pharmaceutical Sciences, Eighteenth Edition (1990), Gennaro, A.R. et al. Editors.*
Lowe, B. L., et. al., In Vitro SAR of (5-(2H)-isoxazolonyl) Ureas, Potent Inhibitors of Hormone-Sensitive Lipase, Bioorganic & Medicinal Chemistry Letters, vol. 14, (2004), pp. 3155-3159.
Bowden, K., et al., The Synthesis of Pantherine and Related Compounds, J. Chem. Soc., (1968), pp. 172-185.

* cited by examiner

*Primary Examiner* — Dennis Heyer
(74) *Attorney, Agent, or Firm* — Morrison & Foerster LLP

(57) ABSTRACT

The present invention relates to 5-oxoisoxazole derivatives of the formula I, the pharmaceutically usable salts thereof and the use thereof as medicinal substances.

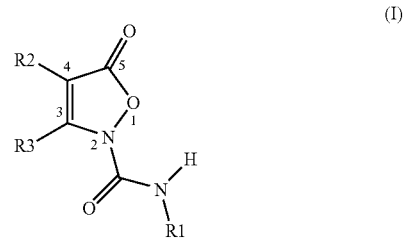

(I)

10 Claims, No Drawings

5-OXOISOXAZOLES AS INHIBITORS OF LIPASES AND PHOSPHOLIPASES

The present invention relates to 5-oxoisoxazoles of the formula I, the pharmaceutically usable salts thereof and the use thereof as medicinal substances.

Certain 3-oxo-3H-benzo[c]isoxazole-1-carboxamides are described as acylpeptidase hydrolase inhibitors in WO 01/44211.

Lowe et al., Bioorg. Med. Chem. Lett. 14 (2004) 3155-3159 describe 3-oxoisoxazole-5-urea derivatives having activity on hormone-sensitive lipase.

Mentioned examples having hydrogen on the urea amino group are described as having no activity on hormone-sensitive lipase. Said examples have no activity on endothelial lipase either.

Compounds with an inhibitory effect on endothelial lipase are described in the prior art, for example in WO2004/094394, WO2004/094393, WO2004/093872 or WO2006/111321.

The invention was based on the object of providing novel compounds which display a therapeutically utilizable effect. The object was in particular to find novel compounds which are suitable for the treatment of elevated blood lipid concentrations, the metabolic syndrome, diabetes, insulin resistance, dysregulation of LDL, HDL or cardiovascular disorders.

It is an object of the present invention to provide compounds which bring about an inhibition of endothelial lipase.

The invention relates to 5-oxoisoxazoles of the formula I

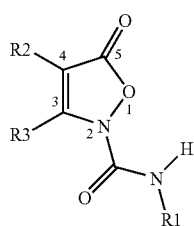

in which the meanings are:
R1 $(C_5-C_{16})$-alkyl, Y-aryl, Y-heteroaryl,
where aryl or heteroaryl may be substituted one or more times by F, Cl, Br, I, OH, $CF_3$, $NO_2$, CN, $OCF_3$, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_4)$-haloalkyl, O—$(C_2$-$C_4)$-haloalkyl, $(C_2$-$C_6)$-alkenyl, $(C_3$-$C_8)$-cycloalkyl, O—$(C_3$-$C_8)$— cycloalkyl, $(C_2$-$C_6)$-alkynyl, $(C_0$-$C_8)$-alkylene-aryl, O—$(C_0$-$C_8)$-alkylene-aryl, S-aryl, $(C_0$-$C_8)$-alkylene-heteroaryl, N(R4)(R5), $SO_2$—$CH_3$, $SO_2$—$NH_2$, $SF_5$, COOH, COO—$(C_1$-$C_6)$-alkyl, CON(R6)(R7), N(R8)CO(R9), N(R10)$SO_2$(R11), CO(R12), (CR13R14)$_x$—O(R15), O—CO—N(R16)(R17), O—CO—$(C_1$-$C_6)$-alkylene-CO—O—$(C_1$-$C_6)$-alkyl, O—CO—$(C_1$-$C_6)$-alkylene-CO—OH, O—CO—$(C_1$-$C_6)$-alkylene-CO—N(R18)(R19), where aryl or heteroaryl may in turn be substituted one or more times by F, Cl, Br, I, OH, $CF_3$, $NO_2$, CN, $OCF_3$, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_4)$-haloalkyl, $(C_2$-$C_6)$-alkenyl, $(C_3$-$C_8)$-cycloalkyl, O—$(C_3$-$C_8)$-cycloalkyl, $(C_2$-$C_6)$-alkynyl, N(R4a)(R5a), $SO_2$—$CH_3$, $SF_5$, COOH, COO—$(C_1$-$C_6)$-alkyl, CON(R6a)(R7a), N(R8a)CO(R9a), N(R10a)$SO_2$(R11a), CO(R12a), (CR13aR14a)$_x$-O(R15a), O—CO—N(R16a)(R17a), O—CO—$(C_1$-$C_6)$-alkylene-CO—O—$(C_1$-$C_6)$-alkyl, O—CO—$(C_1$-$C_6)$-alkylene-CO—OH, O—CO—$(C_1$-$C_6)$-alkylene-CO—N(R18a)(R19a);

x, x' 0, 1, 2, 3, 4, 5, 6;
R4, R5, R6, R7, R9, R10, R11, R12, R13, R14, R15, R16, R17, R18, R19, R4a, R5a, R6a, R7a, R9a, R10a, R11a, R12a, R13a, R14a, R15a, R16a, R17a, R18a, R19a
independently of one another hydrogen, $(C_1$-$C_8)$-alkyl;
or a radical of the formula Ia

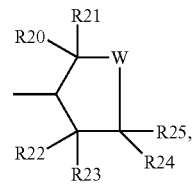

with
W —C(R26)(R27)-, —C(R26)(R27)-C(R28)(R29)-, —C(R26)(R27)-O—;
R20, R21, R22, R23, R24, R25, R26, R27, R28, R29
identically or differently hydrogen, F, Cl, Br, I, OH, $CF_3$, $NO_2$, CN, $OCF_3$, $SF_5$, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_4)$-haloalkyl, O—$(C_2$-$C_4)$-haloalkyl, $(C_2$-$C_6)$-alkenyl, $(C_3$-$C_8)$-cycloalkyl, O—$(C_3$-$C_8)$-cycloalkyl, $(C_3$-$C_8)$-cycloalkenyl, $(C_2$-$C_6)$-alkynyl, N(R30)(R31), $SO_2$—$CH_3$, COOH, COO—$(C_1$-$C_6)$-alkyl, CON(R32)(R33), N(R34)CO(R35), N(R36)$SO_2$(R37), CO(R38), (CR39R40)$_{x''}$—O(R41), O—CO—N(R42)(R43), O—CO—$(C_1$-$C_6)$-alkylene-CO—O—$(C_1$-$C_6)$-alkyl, O—CO—$(C_1$-$C_6)$-alkylene-CO—OH, O—CO—$(C_1$-$C_6)$-alkylene-CO—N(R44)(R45);
x'' 0, 1, 2, 3, 4, 5, 6;
R30, R31, R32, R33, R34, R35, R36, R37, R38, R39, R40, R41, R42, R43, R44, R45
identically or differently hydrogen, $(C_1$-$C_6)$-alkyl; or
R20 and R26 or R21 and R27 together with the carbon atoms carrying them form a monocyclic, 5 or 6 membered saturated, partly unsaturated or aromatic ring system whose individual members may be replaced by —CHR46-, —CR46R47-, =(C—R46)-; or
R22 and R24, or R23 and R25 together with the carbon atoms carrying them form a monocyclic, 5 or 6 membered saturated, partly unsaturated or an aromatic ring system whose individual members may be replaced by —CHR46-, —CR46R47-, =(C—R46)-;
R46, R47 identically or differently F, Cl, Br, I, OH, $CF_3$, $NO_2$, CN, $OCF_3$, $SF_5$, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_4)$-haloalkyl, O—$(C_2$-$C_4)$-haloalkyl, $(C_2$-$C_6)$-alkenyl, $(C_3$-$C_8)$-cycloalkyl, O—$(C_3$-$C_8)$-cycloalkyl, $(C_2$-$C_6)$-alkynyl, N(R48)(R49), $SO_2$—$CH_3$, COOH, COO—$(C_1$-$C_6)$-alkyl, CON(R50)(R51), N(R52)CO(R53), N(R54)$SO_2$(R55), CO(R56), (CR57R58)$_{x'''}$-O(R59), O—CO—N(R60)(R61), O—CO—$(C_1$-$C_6)$-alkylene-CO—O—$(C_1$-$C_6)$-alkyl, O—CO—$(C_1$-$C_6)$-alkylene-CO—OH, O—CO—$(C_1$-$C_6)$-alkylene-CO—N(R62)(R63);
x''' 0, 1, 2, 3, 4, 5, 6;
R48, R49, R50, R51, R52, R53, R54, R55, R56, R57, R58, R59, R60, R61, R62, R63
identically or differently hydrogen, $(C_1$-$C_6)$-alkyl;
Y, Z identically or differently $(C_1$-$C_2)$-alkylene, which may be substituted once by F, Cl, $CH_3$ or OH;

R2 hydrogen, $(C_1-C_{12})$-alkyl, Z-aryl, where aryl may optionally be substituted, $(C_3-C_{12})$-cycloalkyl;

R3 $(C_1-C_{12})$-alkyl, aryl, heteroaryl, where aryl or heteroaryl may optionally be substituted, $(C_3-C_{12})$-cycloalkyl; or R2 and R3 together with the carbon atoms carrying them form a monocyclic, saturated or partly unsaturated 4- to 8-membered ring system whose individual members may be replaced by one to three atoms or atomic groups from the series —CHR64-, —CR64R65-, =(C—R66)-, —NR67-, —C(=O)—, —O—, with the proviso that two units from the series —O— may not be adjacent;

R64, R65, R66, R67 identically or differently hydrogen, F, Cl, Br, I, OH, $CF_3$, $NO_2$, CN, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, N(R68)(R69), $SO_2$—$CH_3$, COOH, COO—$(C_1-C_6)$-alkyl, CON(R70)(R71), N(R72)CO(R73), N(R74)$SO_2$(R75), CO(R76), $(CR77R78)_{x''''}$—O(R79), O—CO—N(R80)(R81), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R82)(R83);

x'''' 0, 1, 2, 3, 4, 5, 6;

R68, R69, R70, R71, R72, R73, R74, R75, R76, R77, R78, R79, R80, R81, R82, R83 identically or differently hydrogen, $(C_1-C_6)$-alkyl;

with the proviso that the compound with R1=cyclohexyl, R2=H and R3=phenyl is excluded;

the tautomeric forms of the compounds and the physiologically tolerated salts thereof.

Preference is given to compounds of the formula I in which

R1 $(C_5-C_{12})$-alkyl, Y-phenyl, Y-heteroaryl, where heteroaryl comprises 1 heteroatom from the series N, O, S, and where phenyl or heteroaryl may be substituted one or more times by F, Cl, Br, OH, $CF_3$, $NO_2$, CN, $OCF_3$, O—$(C_1-C_6)$-alkyl, S—$(C_1-C_6)$-alkyl, $(C_1-C_6)$-alkyl, $(C_2-C_4)$-haloalkyl, $(C_3-C_8)$-cycloalkyl, $(C_0-C_6)$-alkylene-phenyl, O—$(C_0-C_6)$-alkylene-phenyl, S-phenyl, $(C_0-C_8)$-alkylene-heteroaryl, N(R4)(R5), COOH, COO—$(C_1-C_6)$-alkyl, CON(R6)(R7), CO(R12), where phenyl or heteroaryl may in turn be substituted one or more times by F, Cl, OH, $CF_3$, $NO_2$, CN, $OCF_3$, O—$(C_1-C_6)$-alkyl, S—$(C_1-C_6)$-alkyl, $(C_1-C_6)$-alkyl, $(C_2-C_4)$-haloalkyl, $(C_3-C_8)$-cycloalkyl, N(R4a)(R5a), COOH, COO—$(C_1-C_6)$-alkyl, CON(R6a)(R7a) CO(R12a);

x, x' 0, 1, 2, 3, 4, 5, 6;

R4, R5, R6, R7, R12, R4a, R5a, R6a, R7a, R12a, identically or differently hydrogen, $(C_1-C_8)$-alkyl;

or a radical of the formula Ib

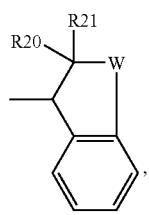

with

W —C(R26)(R27)-, —C(R26)(R27)-C(R28)(R29)-, —C(R26)(R27)-O—;

R20, R21, R26, R27, R28, R29 identically or differently hydrogen, F, Cl, OH, $CF_3$, $NO_2$, CN, $OCF_3$, O—$(C_1-C_6)$-alkyl, $(C_1-C_6)$-alkyl, CO—$(C_1-C_6)$-alkyl; or R20, R21, R26 and R27 together with the carbon atoms carrying them form a fused benzene residue which may be substituted one or more times by F, Cl, CN, $NO_2$, $CF_3$, $OCF_3$, $(C_1-C_6)$-alkyl, O—$(C_1-C_6)$-alkyl, CO—$(C_1-C_6)$-alkyl;

Y, Z identically or differently —$CH_2$— or —$CH_2$—$CH_2$—, which may be substituted once by $CH_3$ or OH;

R2 hydrogen, $(C_1-C_{12})$-alkyl, Z-phenyl, where phenyl may optionally be substituted, $(C_3-C_{12})$-cycloalkyl;

R3 $(C_1-C_{12})$-alkyl, phenyl, heteroaryl, which comprises 1 heteroatom from the series N, O, S, where phenyl or heteroaryl may optionally be substituted, $(C_3-C_{12})$-cycloalkyl; or R2 and R3 together with the carbon atoms carrying them form a monocyclic, saturated 5- to 7-membered ring system whose individual members may be replaced by one to three atomic groups from the series —CHR64-, —CR64R65-, =(C—R66)-;

R64, R65, R66 identically or differently F, Cl, OH, $CF_3$, O—$(C_1-C_6)$-alkyl, O—$(C_1-C_4)$-alkoxy-$(C_1-C_4)$-alkyl, $(C_1-C_6)$-alkyl, $(C_2-C_4)$-haloalkyl, $(C_3-C_8)$-cycloalkyl, N(R68)(R69), $SO_2$—$CH_3$, COOH, COO—$(C_1-C_6)$-alkyl, CON(R70)(R71), N(R72)CO(R73), CO(R76), O—CO—N(R80)(R81), O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—N(R82)(R83);

R68, R69, R70, R71, R72, R73, R76, R77, R78, R79, R80, R81, R82, R83 independently of one another hydrogen, $(C_1-C_6)$-alkyl;

the tautomeric forms of the compounds, and the physiologically tolerated salts thereof.

Particular preference is given to compounds of the formula I in which

R1 is $(C_5-C_8)$-alkyl, Y-phenyl, Y-pyridyl, Y-thienyl, Y-furyl, Y-benzothienyl, Y-benzofuryl, where phenyl or the heteroaromatic radical may be substituted once, twice or three times by F, Cl, Br, $CF_3$, CN, $OCF_3$, O—$(C_1-C_6)$-alkyl, $(C_1-C_6)$-alkyl, $(C_3-C_6)$-cycloalkyl, N(R4)(R5), COOH, COO—$(C_1-C_6)$-alkyl, CON(R6)(R7), CO(R12), and may be substituted once by $(C_0-C_1)$-alkylene-phenyl, O—$(C_0-C_1)$-phenyl, pyrazolyl, pyridyl, thienyl, furyl, benzothienyl, benzofuryl, where a heteroaromatic radical or phenyl may in turn be substituted once, twice or three times by F, Cl, Br, $CF_3$, CN, $OCF_3$, O—$(C_1-C_6)$-alkyl, $(C_1-C_6)$-alkyl, $(C_3-C_6)$-cycloalkyl, N(R4a)(R5a), COOH, COO—$(C_1-C_6)$-alkyl, CON(R6a)(R7a), CO(R12a);

R4, R5, R6, R7, R12, R4a, R5a, R6a, R7a, R12a are independently of one another H, $(C_1-C_8)$-alkyl;

or a radical from the group

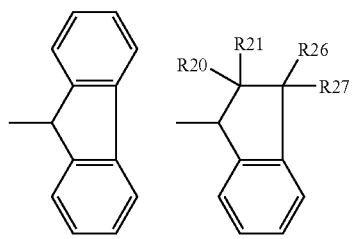

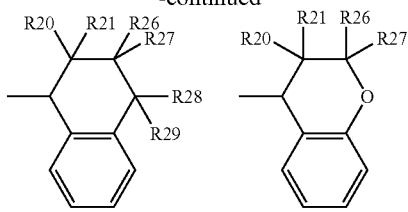
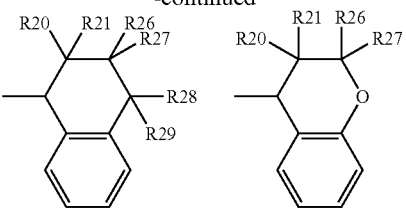

R20, R21, R26, R27, R28, R29 are identically or differently hydrogen, ($C_1$-$C_6$)-alkyl, preferably hydrogen and methyl;

Y is —$CH_2$— or —$CH_2$—$CH_2$—, which may be substituted once by $CH_3$;

R2 is hydrogen, ($C_1$-$C_8$)-alkyl, —$CH_2$-phenyl, where phenyl may optionally be substituted, ($C_3$-$C_8$)-cycloalkyl;

R3 is ($C_1$-$C_8$)-alkyl, phenyl, pyridyl, thienyl, where phenyl, pyridyl or thienyl may optionally be substituted, ($C_3$-$C_8$)-cycloalkyl; or R2 and R3 together with the carbon atoms carrying them form a monocyclic, saturated 6- to 7-membered ring system whose individual members may be replaced by one to three atoms or atomic groups from the series —CHR64-, —CR64R65-;

R64, R65 are identically or differently F, Cl, $CF_3$, $OCF_3$, ($C_1$-$C_6$)-alkyl, O—($C_1$-$C_6$)-alkyl, N(R68)(R69), COOH, COO—($C_1$-$C_6$)-alkyl, CO—N(R70)(R71), CO(R76);

R68, R69, R70, R71, R76 are identically or differently hydrogen, ($C_1$-$C_6$)-alkyl;

the tautomeric forms of the compounds, and the physiologically tolerated salts thereof.

In a particularly preferred embodiment of the compounds of the formula I,
R2 is ispropyl and
R3 is methyl.

In a further particularly preferred embodiment of the compounds of the formula I,
R2 is hydrogen and
R3 is phenyl, which may be substituted once by Cl.

In a further particularly preferred embodiment of the compounds of the formula I,
R2 and R3 together are —$CH_2$—$CH_2$—$CH_2$—$CH_2$— or —$CH_2$—$CH_2$—$CH_2$—$CH_2$—$CH_2$—.

Very particular preference is given to compounds of the formula I in which
R1 is ($C_5$-$C_7$)-alkyl, Y-phenyl, Y-thienyl, Y-benzothienyl, where phenyl or the heteroaromatic radical may be substituted once, twice or three times by F, Cl, Br, $CF_3$, O—$CH_3$, —$CH_3$, —$CH_2CH_3$, —$CH_2$—$CH_2$—$CH_2$—$CH_3$, and be substituted once by phenyl, pyrazolyl or thienyl,
where the heteroaromatic radical or phenyl may in turn be substituted once, twice or three times by F, Cl, Br, $CF_3$, O—($C_1$-$C_6$)-alkyl, ($C_1$-$C_6$)-alkyl;
or a radical from the group

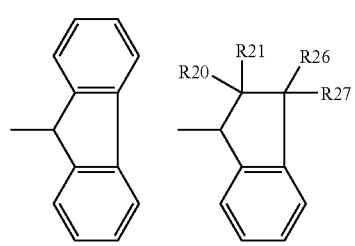

R20, R21, R26, R27, R28, R29 are identically or differently hydrogen, $CH_3$;

Y is —$CH_2$—, which may be substituted once by $CH_3$;

R2 is hydrogen, methyl, isopropyl, cyclopropyl, phenyl, —$CH_2$-phenyl, where phenyl may be substituted by Cl in position 4;

R3 is methyl, phenyl, pyridyl, cyclopropyl, where phenyl may be substituted by Cl; or R2 and R3 are together —$CH_2$—$CH_2$—$CH_2$—$CH_2$— or —$CH_2$—$CH_2$—$CH_2$—$CH_2$—$CH_2$;

the tautomeric forms of the compounds, and the physiologically tolerated salts thereof.

The invention relates to compounds of the formula I in the form of their salts, racemates, racemic mixtures and pure enantiomers, and to their diastereomers and mixtures thereof.

The alkyl radicals in the substituents R1, R2, R3, R4, R5, R6, R7, R9, R10, R11, R12, R13, R14, R15, R16, R17, R18, R19, R4a, R5a, R6a, R7a, R9a, R10a, R11a, R12a, R13a, R14a, R15a, R16a, R17a, R18a, R19a, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, R51, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83 may be either straight chain or branched.

Halogen is fluorine, chlorine, bromine or iodine, preferably fluorine or chlorine. Haloalkyl means an alkyl radical which is substituted one or more times by halogen.

An aryl radical means a phenyl, naphthyl or biphenyl radical.

The preferred aryl radical is phenyl.

The aryl radicals may be substituted one or more times by suitable groups such as, for example: F, Cl, Br, I, $CF_3$, OH, $OCF_3$, $NO_2$, CN, COOH, COO($C_1$-$C_6$)alkyl, $CONH_2$, CONH($C_1$-$C_6$)alkyl, CON[($C_1$-$C_6$)alkyl]$_2$, ($C_3$-$C_{10}$)-cycloalkyl, ($C_1$-$C_{10}$)-alkyl, ($C_2$-$C_6$)-alkenyl, ($C_2$-$C_6$)-alkynyl, O—($C_1$-$C_6$)-alkyl, CO—($C_1$-$C_6$)-alkyl, O—CO—($C_1$-$C_6$)-alkyl, O—CO—($C_1$-$C_6$)-aryl,
$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$, NH—($CH_2$)$_n$-aryl, NH—($CH_2$)$_n$-heterocycle, N(($C_1$-$C_6$)-alkyl)($CH_2$)$_n$-aryl, N(($C_1$-$C_6$)-alkyl)($CH_2$)$_n$-heterocycle, C(NH)($NH_2$), $NH_2$, NH—($C_1$-$C_6$)-alkyl, N(($C_1$-$C_6$)-alkyl)$_2$, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl, $CONH_2$.

Heterocycle is a mono- or bicyclic ring system having 5 to 12 ring members in which at least one atom in the ring system is a heteroatom from the series N, O and S. This definition also includes ring systems in which the heterocycle is fused to a benzene nucleus. $(C_5-C_7)$-heterocycle is a monocyclic, $(C_8-C_{12})$-heterocycle a bicyclic, ring system.

Suitable "heterocyclic rings" or "heterocyclic radicals" are azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl is both 2-, 3- and 4-pyridyl. Thienyl is both 2- and 3-thienyl. Furyl is both 2- and 3-furyl.

Also included are the corresponding N-oxides of these compounds, i.e. for example 1-oxy-2-, 3- or 4-pyridyl.

Heteroaryl is a subgroup of heterocycle and is a mono- or bicyclic aromatic ring system having 5 to 12 ring members, in which at least one atom in the ring system is a heteroatom from the series N, O and S.

Suitable "heteroaryl rings" or "heteroaryl radicals" are for example benzimidazolyl, benzofuranyl, benzothienyl, benzoxazolyl, benzothiazolyl, benzotriazolyl, benzotetrazolyl, benzisoxazolyl, benzisothiazolyl, quinolinyl, furanyl, furazanyl, imidazolyl, 1H-indazolyl, indolyl, 1,2,3-oxadiazolyl, 1,2,4-oxadiazolyl, 1,2,5-oxadiazolyl, 1,3,4-oxadiazolyl, pyrimidinyl, pyrazinyl, pyrazolyl, pyridyl, pyrrolyl, thiazolyl, 1,2,3-thiadiazolyl, 1,2,4-thiadiazolyl, 1,2,5-thiadiazolyl, 1,3,4-thiadiazolyl, thienyl.

Preferred heteroaryl radicals are thienyl, pyridyl, furanyl, pyrazolyl, benzothienyl and benzofuranyl. Particularly preferred heteroaryl radicals are thienyl, benzothienyl and furanyl, and thienyl is especially preferred.

The heterocyclic radicals or the heteroaromatic radicals may be substituted one or more times by suitable groups such as, for example, F, Cl, Br, I, $CF_3$, OH, $OCF_3$, $NO_2$, CN, COOH, COO$(C_1-C_6)$alkyl, $CONH_2$, $CONH(C_1-C_6)$alkyl, $CON[(C_1-C_6)$alkyl$]_2$, $(C_3-C_{10})$-cycloalkyl, $(C_1-C_{10})$-alkyl, $(C_2-C_6)$-alkenyl, $(C_2-C_6)$-alkynyl, O—$(C_1-C_6)$-alkyl, CO—$(C_1-C_6)$-alkyl, O—CO—$(C_1-C_6)$-alkyl, O—CO—$(C_1-C_6)$-aryl, $PO_3H_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N(C_1-C_6)$-alkyl$)(CH_2)_n$-aryl, $SO_2$—$N(C_1-C_6)$-alkyl$)(CH_2)_n$-heterocycle, $SO_2$—$N((CH_2)_n$-aryl$)_2$, $SO_2$—$N((CH_2)_n$-(heterocycle)$)_2$, NH—$(CH_2)_n$-aryl, NH—$(CH_2)_n$-heterocycle, $N((C_1-C_6)$-alkyl$)(CH_2)_n$-aryl, $N((C_1-C_6)$-alkyl$)(CH_2)_n$-heterocycle, $C(NH)(NH_2)$, $NH_2$, NH—$(C_1-C_6)$-alkyl, $N((C_1-C_6)$-alkyl$)_2$, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl, $CONH_2$.

A cycloalkyl radical means a ring system which comprises one or more rings, which is saturated or partly unsaturated (having one or two double bonds) and which is composed exclusively of carbon atoms, such as, for example, cyclopropyl, cyclopentyl, cyclopentenyl, cyclohexyl, cyclohexenyl or adamantyl.

The cycloalkyl radicals may be substituted one or more times by suitable groups such as, for example: F, Cl, Br, I, $CF_3$, OH, $OCF_3$, $NO_2$, CN, COOH, COO$(C_1-C_6)$alkyl, $CONH_2$, $CONH(C_1-C_6)$alkyl, $CON[(C_1-C_6)$alkyl$]_2$, $(C_3-C_{10})$-cycloalkyl, $(C_1-C_{10})$-alkyl, $(C_2-C_6)$-alkenyl, $(C_2-C_6)$-alkynyl, O—$(C_1-C_6)$-alkyl, CO—$(C_1-C_6)$-alkyl, O—CO—$(C_1-C_6)$-alkyl, O—CO—$(C_1-C_6)$-aryl, $PO_3H_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N(C_1-C_6)$-alkyl$)(CH_2)_n$-aryl, $SO_2$—$N(C_1-C_6)$-alkyl$)(CH_2)_n$-heterocycle, $SO_2$—$N((CH_2)_n$-aryl$)_2$, $SO_2$—$N((CH_2)_n$-(heterocycle)$)_2$, NH—$(CH_2)_n$-aryl, NH—$(CH_2)_n$-heterocycle, $N((C_1-C_6)$-alkyl$)(CH_2)_n$-aryl, $N((C_1-C_6)$-alkyl$)(CH_2)_n$-heterocycle, $C(NH)(NH_2)$, $NH_2$, NH—$(C_1-C_6)$-alkyl, $N((C_1-C_6)$-alkyl$)_2$, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl, $CONH_2$.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the invention of the formula I, for example an ester, which on administration to a mammal such as, for example, a human is able to form (directly or indirectly) a compound of the formula I or an active metabolite thereof.

Physiologically functional derivatives also include prodrugs of the compounds of the invention as, for example, described in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

The compounds of the invention of the formula I have a surprising inhibitory effect on endothelial lipase (EL). The preferred substrate for EL is HDL, which has antiatherosclerotic activity. A reduction in the HDL level leads to progression of atherosclerosis and its sequelae such as metabolic syndrome and coronary heart disease. An inhibition of EL should thus lead to prevention of atherosclerotic disorders.

It has further been found that the inhibitory effect of the compounds of the invention of the formula I is selective in relation to other lipases such as, for example, hormone-sensitive lipase (HSL).

The compounds of the formula I additionally show an improved solubility in aqueous media with an activity which is at least as high as that of compounds of similar structures. The compounds of the invention are further distinguished by further advantageous properties such as higher metabolic stability and serum stability compared with prior art compounds.

Compounds of this type are particularly suitable for the treatment and/or prevention of 1. Dyslipidemias and general disorders of lipid metabolism and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations
   low HDL cholesterol concentration
   low apoA lipoprotein concentrations
   high LDL cholesterol concentrations
   small dense LDL cholesterol particles
   high apoB lipoprotein concentrations
2. Various other conditions which may be associated with the metabolic syndrome, such as:
   obesity (excess weight), including central obesity
   thromboses, hypercoagulable and prothrombotic stages (arterial and venous)
   high blood pressure
   heart failure such as, for example (but not restricted thereto), following myocardial infarction, hypertensive heart disease or cardiomyopathy
   diabetes mellitus, especially type 2 diabetes, including the prevention of the sequelae associated therewith (hyperglycemia, glucose intolerance, loss of the pancreatic 11 cells, macro- and microvascular disorders
3. Other disorders or conditions in which inflammatory reactions or cell differentiation is for example involved are:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   pancreatitis
   other inflammatory states
   retinopathy
   adipose cell tumors
   adipose cell carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   acute and chronic myeloproliferative disorders and lymphomas
   angiogenesis
   neurodegenerative disorders
   Alzheimer's disease
   multiple sclerosis
   Parkinson's disease
   erythemato-squamous dermatoses such as, for example, psoriasis
   acne vulgaris
   other skin disorders and dermatological conditions which are modulated by PPAR
   eczemas and neurodermatitis
   dermatitis such as, for example, seborrheic dermatitis or photodermatitis
   keratitis and keratoses such as, for example, seborrheic keratoses, senile keratoses, actinic keratosis, photo-induced keratoses or keratosis follicularis
   keloids and keloid prophylaxis
   warts, including condylomata or condylomata acuminata
   human papilloma viral (HPV) infections such as, for example, venereal papillomata, viral warts such as, for example, molluscum contagiosum, leukoplakia
   papular dermatoses such as, for example, lichen planus
   skin cancer such as, for example, basal-cell carcinomas, melanomas or cutaneous T-cell lymphomas
   localized benign epidermal tumors such as, for example, keratoderma, epidermal naevi
   chilblains
   high blood pressure
   syndrome X
   polycystic ovary syndrome (PCOS)
   asthma
   osteoarthritis
   lupus erythematosus (LE) or inflammatory rheumatic disorders such as, for example, rheumatoid arthritis
   vasculitis
   wasting (cachexia)
   gout
   ischemia/reperfusion syndrome
   acute respiratory distress syndrome (ARDS)

Formulations

The amount of a compound of the invention necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of the invention. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse sequelae thereof.

Combinations with Other Medicaments

The compounds of the invention can be administered alone or in combination with one or more further pharmacologically active ingredients. In particular the compounds of the invention can be administered with active ingredients, which have a similar pharmacological effect to themselves. For example, they can be administered in combination with active ingredients which have favorable effects on metabolic disturbances or disorders frequently associated therewith. Examples of such medicaments are 1. medicaments which lower blood glucose, antidiabetics,
    2. active ingredients for the treatment of dyslipidemias,
    3. antiatherosclerotic medicaments,
    4. antiobesity agents, 5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.
11. active ingredients for the treatment of neurodegenerative diseases
12. active ingredients for the treatment of diseases of the central nervous system
13. active ingredients for the treatment of dependence on drugs, nicotine and alcohol
14. analgesics They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Further active ingredients particularly suitable for the combination products are: All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. They can be combined with the compound of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or Apidra® or those described in WO 2005005477 (Novo Nordisk), fast-acting insulins (see U.S. Pat. No. 6,221,633), inhalable insulins such as, for example, Exubera® or oral insulins such as, for example, 1N-105 (Nobex) or Oral-lyn™ (Generex Biotechnology), GLP-1-derivatives such as, for example, exenatide, liraglutide or those which have been disclosed in WO 98/08871 or WO 2005/027978 of Novo Nordisk NS, in WO 01/04156 of Zealand or in WO 00/34331 of Beaufour-Ipsen, Pramlintide Acetate (Symlin; Amylin Pharmaceuticals), and orally effective hypoglycemic active ingredients.

The active ingredients include preferably
sulfonylureas,
biguanides,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT), GLP-1 agonists,
potassium channel openers such as, for example, those which have been disclosed in WO 97/26265 and WO 99/03861 of Novo Nordisk NS,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMGCoA reductase inhibitor such as simvastatin, fluvastatin, pravastatin, lovastatin, atorvastatin, cerivastatin, rosuvastatin or L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO 2005042692), MD-0727 (Microbia Inc., WO 2005021497) or with compounds as described in WO 2002066464 (Kotobuki Pharmaceutical Co. Ltd.), WO 2005062824 (Merck & Co.) or WO 2005061451 and WO 2005061452 (AstraZeneca AB).

In one embodiment of the invention, the compound of the formula I is administered in combination with a PPAR gamma agonist such as, for example, rosiglitazone, pioglitazone, JTT-501, GI 262570, R-483 or CS-011 (rivoglitazone).

In one embodiment of the invention, the compound of the formula I is administered in combination with a PPAR alpha agonist such as, for example, GW9578, GW-590735, K-111, LY-674, KRP-101 or DRF-10945.

In one embodiment of the invention, the compound of the formula I is administered in combination with a mixed PPAR alpha/gamma agonist such as, for example, muraglitazar, tesaglitazar, naveglitazar, LY-510929, ONO-5129, E-3030 or as described in WO 00/64888, WO 00/64876, WO 03/020269, WO 2004075891, WO 2004076402, WO 2004075815, WO 2004076447, WO 2004076428, WO 2004076401, WO 2004076426, WO 2004076427, WO 2006018118, WO 2006018115, and WO 2006018116 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516, or as described in WO 2005097762, WO 2005097786, WO 2005097763, WO 2006029699.

In one embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate such as, for example, fenofibrate, clofibrate or bezafibrate.

In one embodiment of the invention, the compound of the formula I is administered in combination with an MTP inhibitor such as, for example, implitapide, BMS-201038, R-103757 or those described in WO 2005085226.

In one embodiment of the invention, the compound of the formula I is administered in combination with a CETP inhibitor such as, for example, torcetrapib or JTT-705.

In one embodiment of the invention, the compound of the formula I is administered in combination with a bile acid absorption inhibitor (see, for example, U.S. Pat. No. 6,245,744, U.S. Pat. No. 6,221,897 or WO 00/61568), such as, for example, HMR 1741 or those as described in DE 10 2005 033099.1 and DE 10 2005 033100.9.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO 2005097738.

In one embodiment, the compound of the formula I is administered in combination with Omacor® (Omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494 or as described in WO 2005077907.

In one embodiment of the invention, the compound of the formula I is administered in combination with a lipoprotein (a) antagonist such as, for example, gemcabene (CI-1027).

In one embodiment of the invention, the compound of the formula I is administered in combination with an HM74A receptor agonist such as, for example, nicotinic acid.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment of the invention, the compound of the formula I is administered in combination with a sulfonylurea such as, for example, tolbutamide, glibenclamide, glipizide or glimepiride.

In one embodiment of the invention, the compound of the formula I is administered in combination with a biguanide such as, for example, metformin.

In another embodiment of the invention, the compound of the formula I is administered in combination with a meglitinide such as, for example, repaglinide or nateglinide.

In one embodiment of the invention, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the invention, the compound of the formula I is administered in combination with an α-glucosidase inhibitor such as, for example, miglitol or acarbose.

In one embodiment of the invention, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I is administered in combination with an inhibitor of glycogen phosphorylase, such as, for example, PSN-357 or FR-258900 or those as described in WO 2003084922, WO 2004007455, WO 2005073229-31 or WO 2005067932.

In one embodiment of the invention, the compound of the formula I is administered in combination with glucagon receptor antagonists such as, for example, A-770077, NNC-25-2504 or as described in WO 2004100875 or WO 2005065680.

In one embodiment of the invention, the compound of the formula I is administered in combination with activators of glucokinase, such as, for example, RO-4389620, LY-2121260 (WO 2004063179), PSN-105, PSN-110, GKA-50 or those as are described for example by Prosidion in WO 2004072031, WO 2004072066, WO 05103021 or WO 06016178, by Roche in WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, U.S. Pat. No. 4,067,939 or WO 04052869, by Novo Nordisk in EP 1532980, WO 03055482, WO 04002481, WO 05049019, WO 05066145 or WO 05123132, by Merck/Banyu in WO 03080585, WO 03097824, WO 04081001, WO 05063738 or WO 05090332, by Eli Lilly in WO 04063194, or by Astra Zeneca in WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment of the invention, the compound of the formula I is administered in combination with an inhibitor of gluconeogenesis, such as, for example, FR-225654.

In one embodiment of the invention, the compound of the formula I is administered in combination with inhibitors of fructose-1,6-bisphosphatase (FBPase), such as, for example, CS-917.

In one embodiment of the invention, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I is administered in combination with inhibitors of glutamine-fructose-6-phosphate amidotransferase (GFAT), as are described for example in WO 2004101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964× or as are described in WO 2003074500, WO 2003106456, WO 200450658, WO 2005058901, WO 2005012312, WO 2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I is administered in combination with inhibitors of 11-beta-hydroxysteroid dehydrogenase 1 (11β-HSD1), such as, for example, BVT-2733 or those as are described for example in WO 200190090-94, WO 200343999, WO 2004112782, WO 200344000, WO 200344009, WO 2004112779, WO 2004113310, WO 2004103980, WO 2004112784, WO 2003065983, WO 2003104207, WO 2003104208, WO 2004106294, WO 2004011410, WO 2004033427, WO 2004041264, WO 2004037251, WO 2004056744, WO 2004065351, WO 2004089367, WO 2004089380, WO 2004089470-71, WO 2004089896, WO 2005016877 or WO 2005097759.

In one embodiment of the invention, the compound of the formula I is administered in combination with inhibitors of protein tyrosine phosphatase 1B (PTP1B), as are described for example in WO 200119830-31, WO 200117516, WO 2004506446, WO 2005012295, PCT/EP2005/005311, PCT/EP2005/005321, PCT/EP2005/007151, PCT/EP2005/01294 or DE 10 2004 060542.4.

In one embodiment of the invention, the compound of the formula I is administered in combination with modulators of the sodium-dependent glucose transporter 1 or 2 (SGLT1, SGLT2), such as, for example, KGA-2727, T-1095 and SGL-0010 or as are described for example in WO 2004007517, WO 200452903, WO 200452902, WO 2005121161, WO 2005085237, JP2004359630 or by A. L. Handlon in Expert Opin. Ther. Patents (2005) 15(11), 1531-1540.

In one embodiment of the invention, the compound of the formula I is administered in combination with inhibitors of hormone-sensitive lipase (HSL) as described for example in WO 01/17981, WO 01/66531, WO 2004035550, WO 2005073199 or WO 03/051842.

In one embodiment of the invention, the compound of the formula I is administered in combination with inhibitors of acetyl-CoA carboxylase (ACC), such as, for example, those as described in WO 199946262, WO 200372197, WO 2003072197 or WO 2005044814.

In one embodiment of the invention, the compound of the formula I is administered in combination with an inhibitor of phosphoenolpyruvate carboxykinase (PEPCK), such as, for example, those as described in WO 2004074288.

In one embodiment of the invention, the compound of the formula I is administered in combination with an inhibitor of glycogen synthase kinase 3 beta (GSK-3 beta), as described for example in US2005222220, WO 2004046117, WO 2005085230, WO 2005111018, WO 2003078403, WO 2004022544, WO 2003106410, WO 2005058908, US2005038023, WO 2005009997, US2005026984, WO 2005000836, WO 2004106343, EP1460075, WO 2004014910, WO 2003076442, WO 2005087727 or WO 2004046117.

In one embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin A receptor antagonist such as, for example, avosentan (SPP-301).

In one embodiment of the invention, the compound of the formula I is administered in combination with inhibitors of "I-kappaB kinase" (IKK inhibitors), as are described for example in WO 2001000610, WO 2001030774, WO 2004022553 or WO 2005097129.

In one embodiment of the invention, the compound of the formula I is administered in combination with modulators of the glucocorticoid receptor, like those described for example in WO 2005090336.

In a further embodiment of the invention, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, naphthalene-1-sulfonic acid {4-[(4-amino-quinazolin-2-ylamino)methyl]cyclohexylmethyl}amide hydrochloride (CGP 71683A);

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO 2005080424;

cannabinoid receptor 1 antagonists such as, for example, rimonabant, SR147778 or those as are described for example in EP 0656354, WO 00/15609, WO 02/076949, WO 2005080345, WO 2005080328, WO 2005080343, WO 2005075450, WO 2005080357, WO 200170700, WO 2003026647-48, WO 200302776, WO 2003040107, WO 2003007887, WO 2003027069, U.S. Pat. No. 6,509,367, WO 200132663, WO 2003086288, WO 2003087037, WO 2004048317, WO 2004058145, WO 2003084930, WO 2003084943, WO 2004058744, WO 2004013120, WO 2004029204, WO 2004035566, WO 2004058249, WO 2004058255, WO 2004058727, WO 2004069838, US20040214837, US20040214855, US20040214856, WO 2004096209, WO 2004096763, WO 2004096794, WO 2005000809, WO 2004099157, US20040266845, WO 2004110453, WO 2004108728, WO 2004000817, WO 2005000820, US20050009870, WO 200500974, WO 2004111033-34, WO 200411038-39, WO 2005016286, WO 2005007111, WO 2005007628, US20050054679, WO 2005027837, WO 2005028456, WO 2005063761-62, WO 2005061509 or WO 2005077897;

MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO 2005060985, WO 2005009950, WO 2004087159, WO 2004078717, WO 2004078716, WO 2004024720, US20050124652, WO 2005051391, WO 2004112793, WOUS20050222014, US20050176728, US20050164914, US20050124636, US20050130988, US20040167201, WO 2004005324, WO 2004037797, WO 2005042516, WO 2005040109, WO 2005030797, US20040224901, WO 200501921, WO 200509184, WO 2005000339, EP1460069, WO 2005047253, WO 2005047251, EP1538159, WO 2004072076, WO 2004072077 or WO 2006024390;

orexin receptor antagonists (e.g. 1-(2-methylbenzoxazol-6-yl)-3-[1,5]naphthyridin-4-ylurea hydrochloride (SB- 334867-A) or those as are described for example in WO 200196302, WO 200185693, WO 2004085403 or WO 2005075458);

histamine H3 receptor agonists (e.g. 3-cyclohexyl-1-(4,4-dimethyl-1,4,6,7-tetrahydro-imidazo[4,5-c]pyridin-5-yl) propan-1-one oxalic acid salt (WO 00/63208) or those as are described in WO 200064884, WO 2005082893);

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);

urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO 2003/15769, WO 2005085200, WO 2005019240, WO 2004011438, WO 2004012648, WO 2003015769, WO 2004072025, WO 2005070898, WO 2005070925, WO 2006018280, WO 2006018279, WO 2004039780, WO 2003033476, WO 2002006245, WO 2002002744, WO 2003004027 or FR2868780);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (e.g. dexfenfluramine);

mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

5-HT2C receptor agonists (such as, for example, APD-356, BVT-933 or those as are described in WO 200077010, WO 20077001-02, WO 2005019180, WO 2003064423, WO 200242304 or WO 2005082859);

5-HT6 receptor antagonists as are described for example in WO 2005058858;

bombesin receptor agonists (BRS-3 agonists);

galanin receptor antagonists;

growth hormone (e.g. human growth hormone or AOD-9604);

growth hormone releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO 2005030734;

TRH agonists (see, for example, EP 0 462 884);

uncoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (like those described for example in WO 00/40569);

inhibitors of diacylglycerol O-acyltransferases (DGATs) as described for example in US2004/0224997, WO 2004094618, WO 200058491, WO 2005044250, WO 2005072740, JP2005206492 or WO 2005013907;

inhibitors of fatty acid synthase (FAS) such as, for example, C75 or those as described in WO 2004005277;

oxyntomodulin;

oleoyl-estrone or thyroid hormone receptor agonists such as, for example: KB-2115 or those as described in WO 20058279, WO 200172692, WO 200194293, WO 2003084915, WO 2004018421 or WO 2005092316.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindole or phentermine.

In one embodiment of the invention, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6)). Caromax is a carob-containing product from Nutrinova, Nutrition Specialties & Food Ingredients GmbH, Industriepark Hoechst, 65926 Frankfurt/Main. Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compound of the formula I is administered in combination with PDE inhibitors (phosphodiesterase), like those described for example in WO 2003/077949 or WO 2005012485.

In one embodiment of the invention, the compound of the formula I is administered in combination with NAR-1 (nicotinic acid receptor) agonists like those described for example in WO 2004094429.

In one embodiment of the invention, the compound of the formula I is administered in combination with CB2 (cannabinoid receptor) agonists like those described for example in US2005/143448.

In one embodiment of the invention, the compound of the formula I is administered in combination with histamine 1 agonists like those described for example in WO 2005101979.

In one embodiment of the invention, the compound of the formula I is administered in combination with bupropion as described in WO 2006017504.

In one embodiment of the invention, the compound of the formula I is administered in combination with opioid antagonists like those described for example in WO 2005107806 or WO 2004094429.

In one embodiment of the invention, the compound of the formula I is administered in combination with neutral endopeptidase inhibitors like those described for example in WO 200202513, WO 2002/06492, WO 2002040008, WO 2002040022 or WO 2002047670.

In one embodiment of the invention, the compound of the formula I is administered in combination with NPY inhibitors (neuropeptide Y) like those described for example in WO 2002047670.

In one embodiment of the invention, the compound of the formula I is administered in combination with sodium/hydrogen exchange inhibitors like those described for example in WO 2003092694.

In one embodiment of the invention, the compound of the formula I is administered in combination with modulators of the glucocorticoid receptor like those described for example in WO 2005090336.

In one embodiment of the invention, the compound of the formula I is administered in combination with nicotine receptor agonists like those described for example in WO 2004094429.

In one embodiment of the invention, the compound of the formula I is administered in combination with NRIs (norepinephrine reuptake inhibitors) like those described for example in WO 2002053140.

In one embodiment of the invention, the compound of the formula I is administered in combination with MOA (E-beta-methoxyacrylate) such as, for example, segeline or like those described for example in WO 2002053140.

In one embodiment of the invention, the compound of the formula I is administered in combination with antithrombotic active ingredients such as, for example, clopidrogel.

It will be appreciated that every suitable combination of the compounds of the invention with one or more of the aforementioned compounds and optionally one or more other pharmacologically active substances is regarded as falling within the protection conferred by the present invention.

Some of the formulae for the development codes mentioned above are detailed hereinafter.

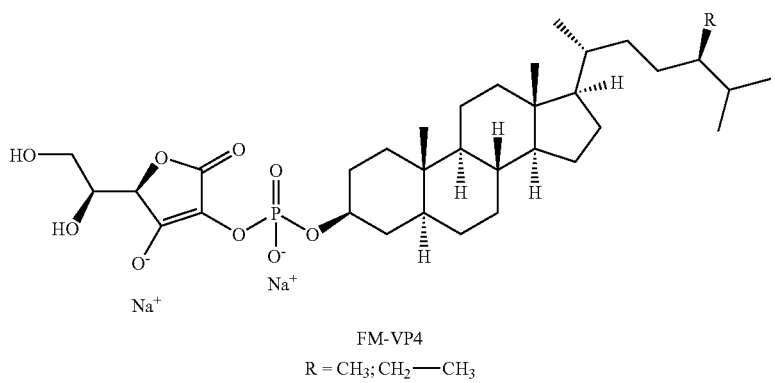

FM-VP4
R = CH$_3$; CH$_2$—CH$_3$

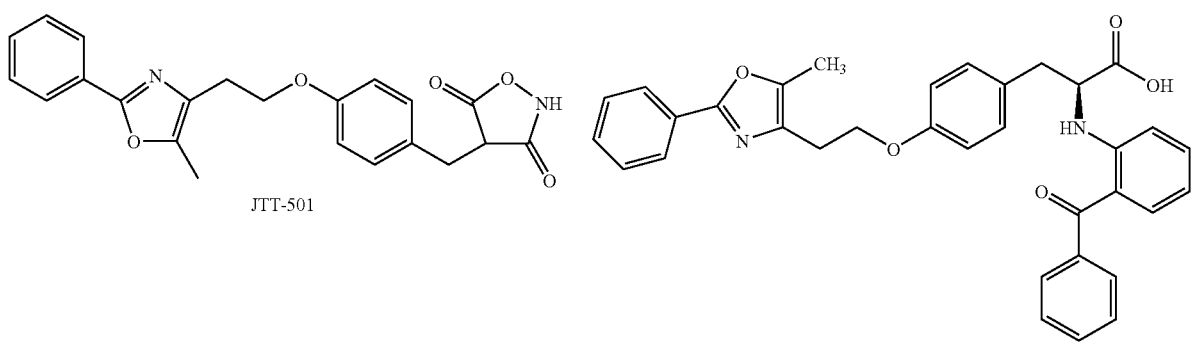

JTT-501

GI 262570

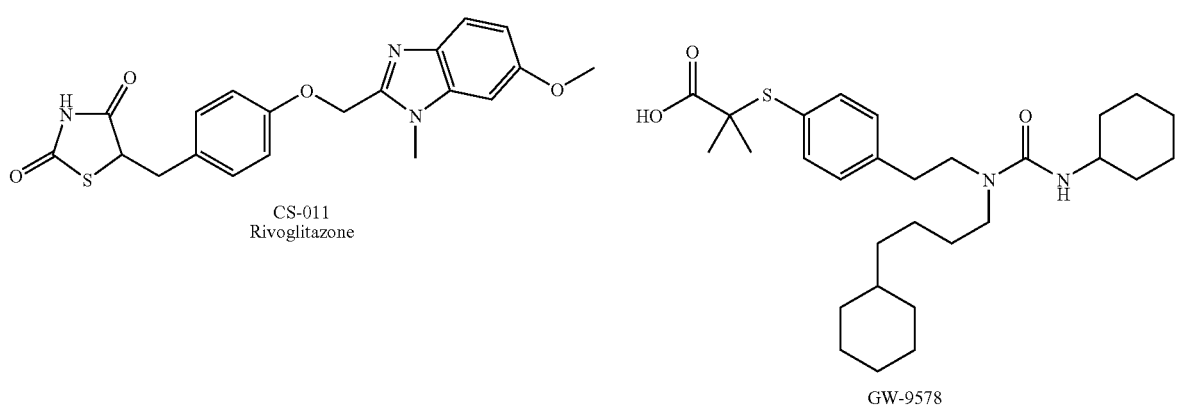

CS-011
Rivoglitazone

GW-9578

-continued
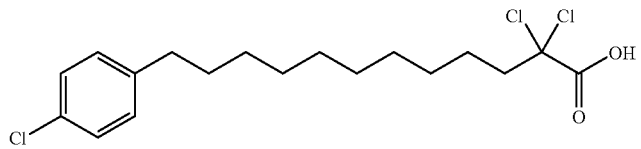
K-111
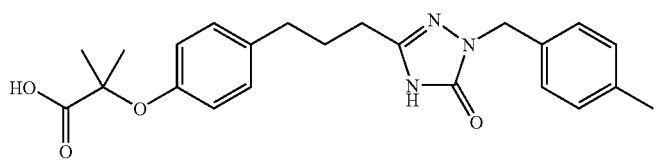
LY-674
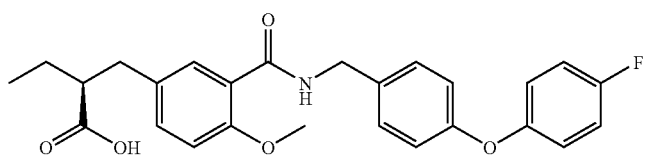
KRP-101
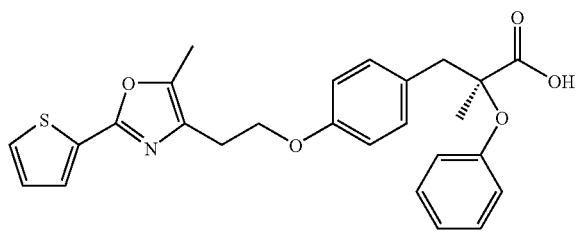
LY-510929
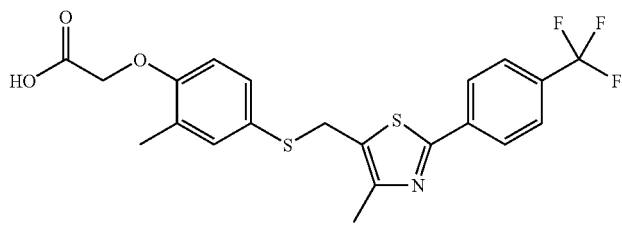
GW-501516
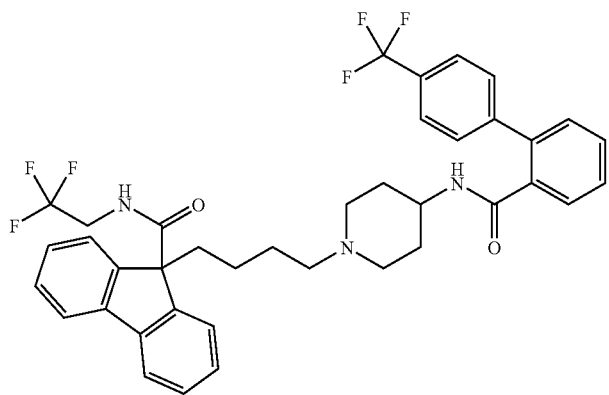
BMS-201038

-continued
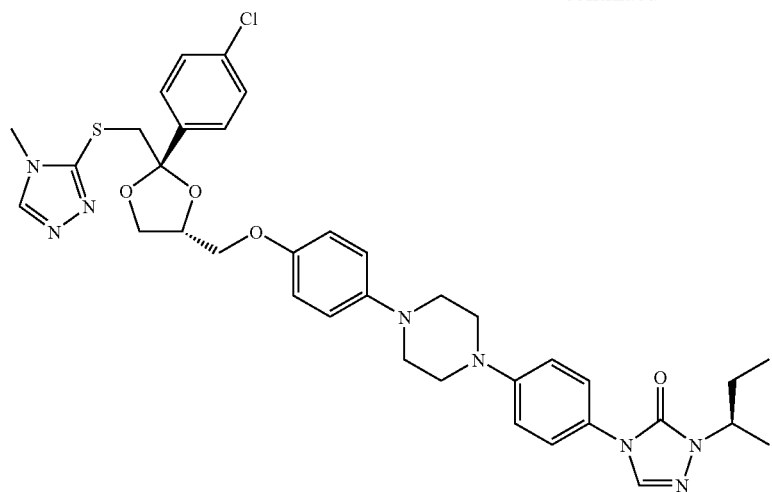
R-103757
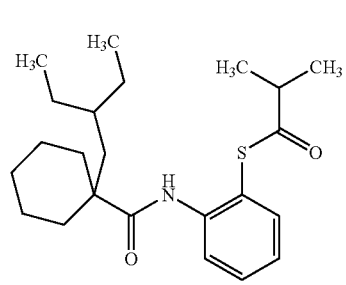
JTT-705
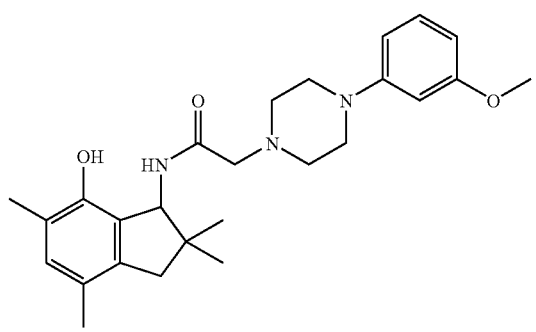
OPC-14117
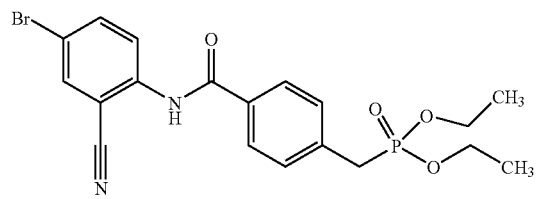
NO-1886
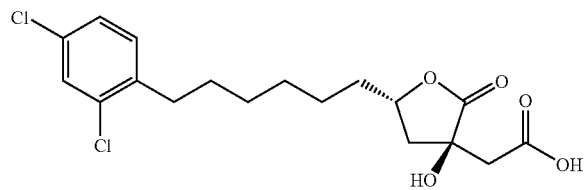
SB-204990
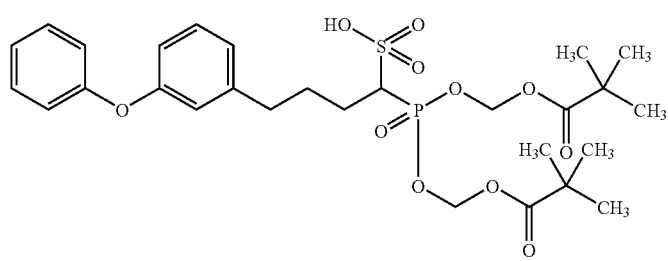
BMS-188494
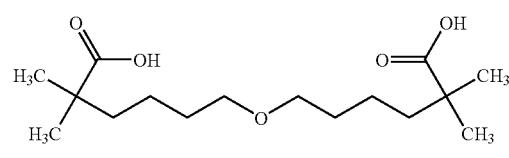
CI-1027
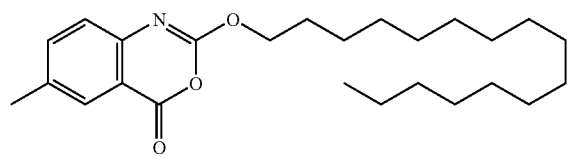
ATL-962

-continued
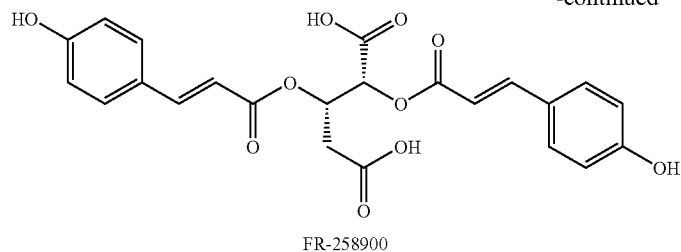
FR-258900
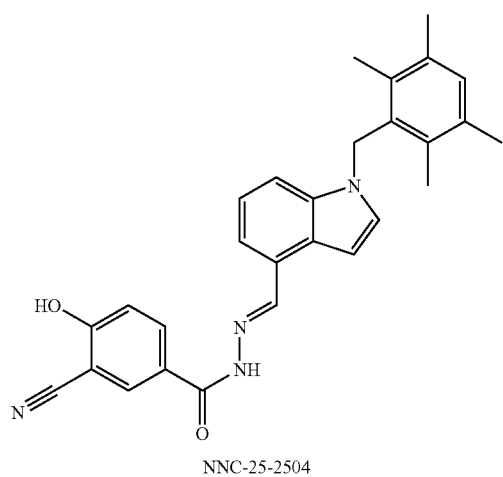
NNC-25-2504
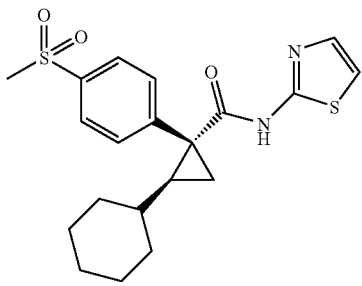
LY-2121260
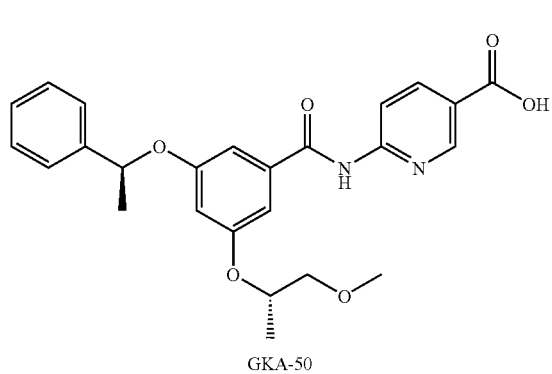
GKA-50
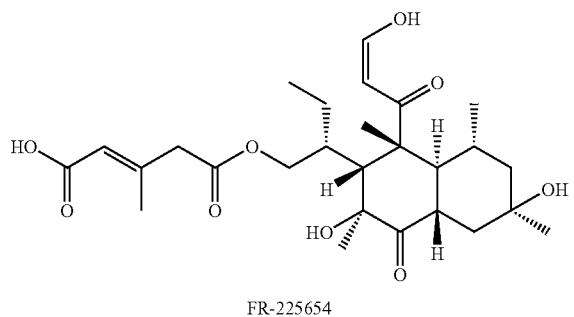
FR-225654
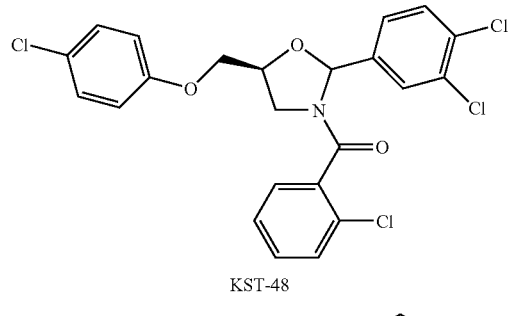
KST-48
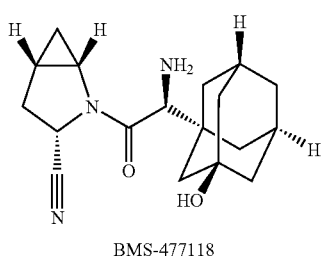
BMS-477118
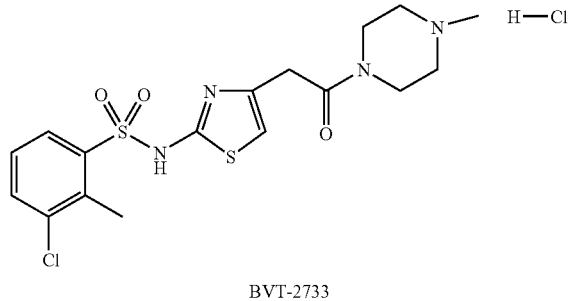
BVT-2733
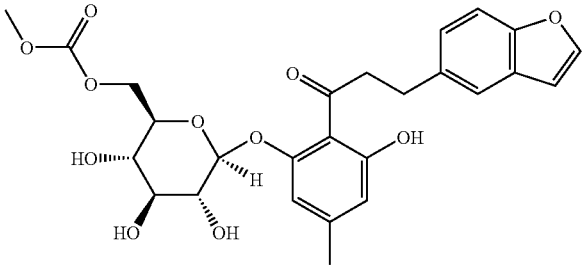
T-1095

-continued
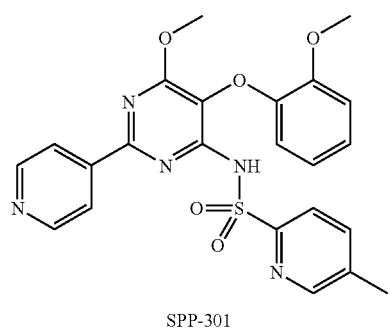
SPP-301
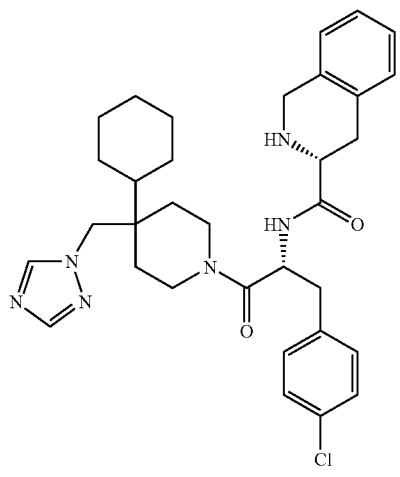
THIQ
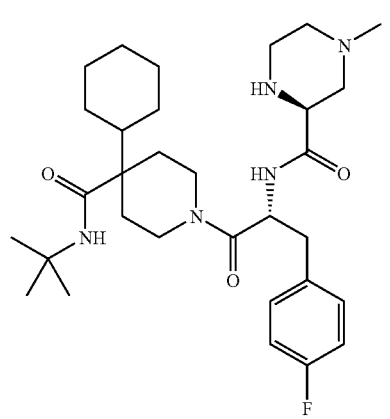
MB243
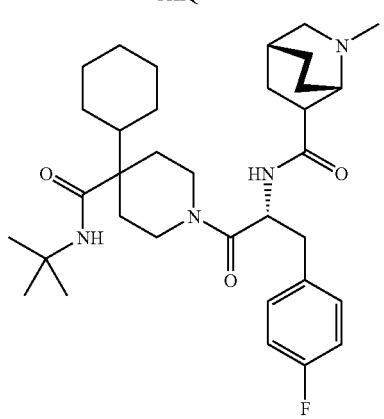
RY764
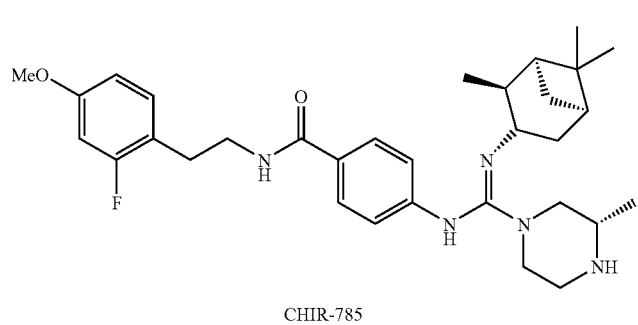
CHIR-785
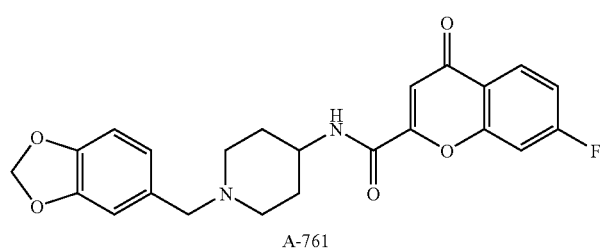
A-761
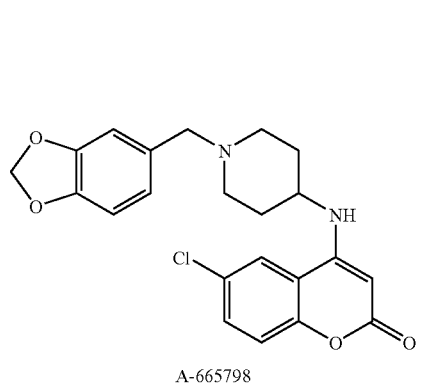
A-665798

-continued
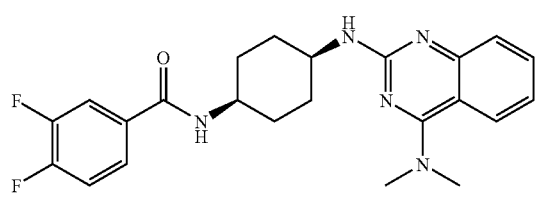
ATC-0175
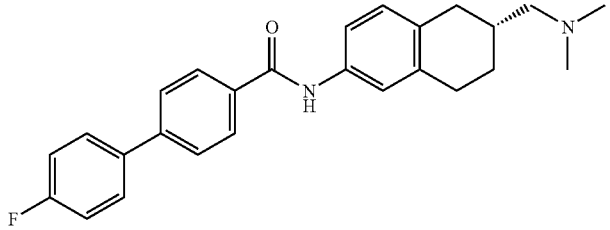
T-226296
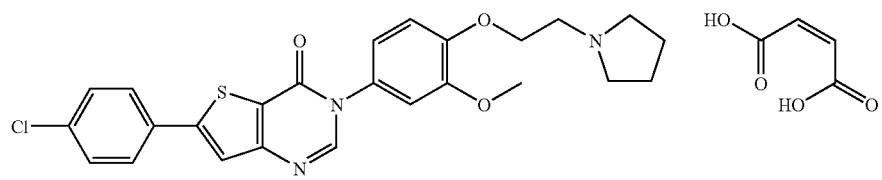
GW-803430
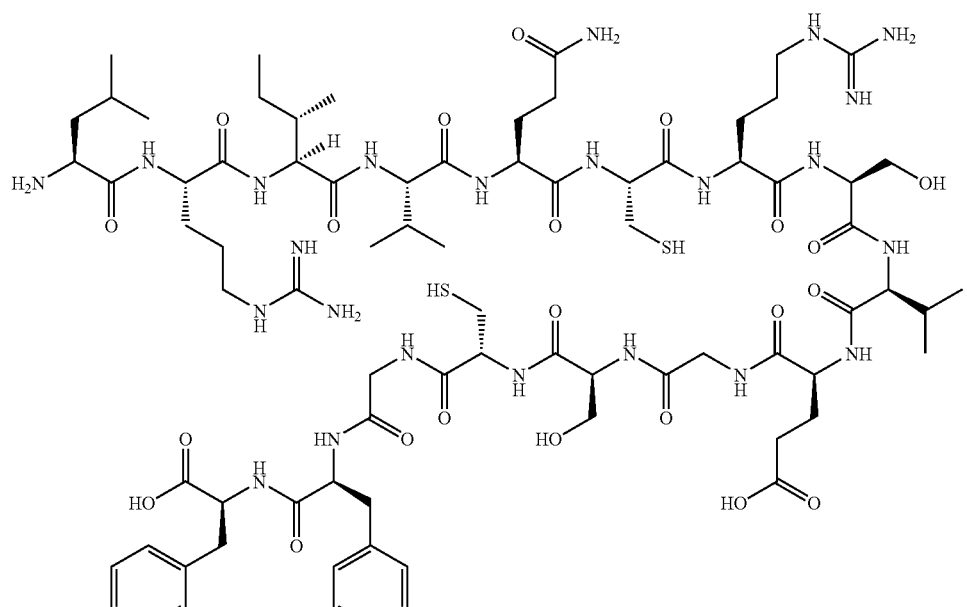
AOD-9604
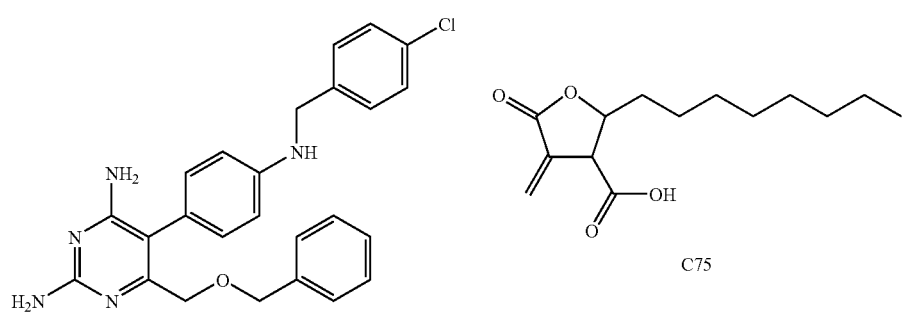
A-778193
C75

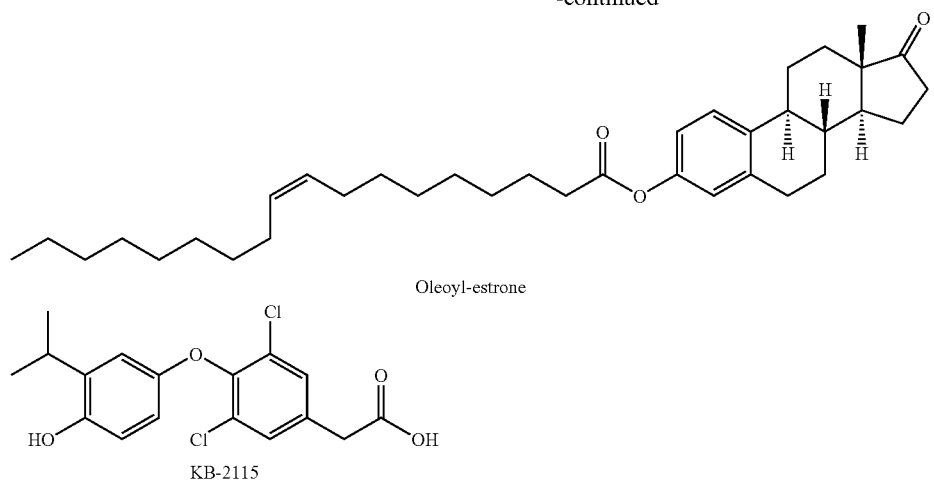

Oleoyl-estrone

KB-2115

The activity of the compounds of the invention of the formula I was tested in the following enzyme assay system:

EL Inhibition Assay:

EL is released as secretory protein in high concentration into cell culture medium (conditioned medium) by recombinant cell lines (CHO, HEK293). This is employed as enzyme solution after concentration.

EL Activity Assay

The phospholipase-specific substrate 1,2-bis(4,4-difluoro-5,7-dimethyl-4-bora-3a,4a-diaza-s-indacene-3-undecanoyl)-sn-glycero-3-phosphocholine, (manufacturer Molecular Probes) is used to characterize the enzymatic activity of endothelial lipase and the effect of inhibitors. Hydrolysis of the A1 ester linkage of this phospholipid by the enzyme liberates a fatty acid labeled by the fluorescent dye Bodipy which can be detected after separation by thin-layer chromatography on an HPTLC plate (silica gel 60, Merck) or directly in the reaction vessel by measuring the fluorescence.

The substrate solution is prepared by dissolving 100 μg of 1,2-bis(4,4-difluoro-5,7-dimethyl-4-bora-3a,4a-diaza-s-indacene-3-undecanoyl)-sn-glycero-3-phosphocholine (manufacturer Molecular Probes) in 100 μl DMSO and taking it up in 2.4 mg of tripalmitin (Sigma) in 393 μl chloroform which contains 20 mg/ml DOP-choline (1,2-dioleoyl-sn-glycero-3-phosphocholine). 39.3 μl of this lipid mixture are transferred into a fresh reaction vessel and the solvent is evaporated. The lipid mixture is dissolved in 4 ml of 200 mM TRIS-HCl, 150 mM sodium chloride, pH=7.4, by sonication twice. The subsequent enzymic reaction takes place at 37° C. for 90 minutes. For this purpose, 20 μl of the substrate solution are incubated with 2 μl of inhibitor of appropriate concentration (dissolved in 10% DMSO, 10% strength DMSO solution is used as control) and 2 μl of enzyme solution (conditioned medium). Then 4 μl of the assay mixture are loaded onto an HPTLC plate (silica gel 60, Merck), and the liberated fluorescent dye is separated for detection with an eluent (diethyl ether:petroleum benzine:acetic acid [78:22:1]). After evaporation of the eluent, the plate is read in a fluorescence scanner. An increased release of the fluorescent dye in the uninhibited reaction is to be observed as a measure of the enzymic activity.

The enzymatic activity is reduced as a function of the inhibitor concentration used, and the inhibitor concentration at which a half-maximum enzymic activity is observed is called $IC_{50}$.

| Example | $IC_{50}$ [μM] EL |
|---|---|
| 6 | 0.028 |
| 7 | 0.9 |
| 8 | 3.2 |
| 10 | 0.06 |
| 16 | 0.004 |
| 18 | 14.1 |
| 25 | 0.009 |
| 26 | 0.035 |
| 31 | 0.1 |
| 39 | 0.001 |
| 40 | 0.053 |
| 44 | 0.5 |

Other Test Models

The suitability of the compounds of the invention as active pharmaceutical ingredient can be tested by means of various test models. Descriptions of such test models are given below by way of example.

Solubility in Aqueous Systems

Adequate solubility of a substance in aqueous solvent systems is an important prerequisite for a (reproducible) pharmacological effect. Solubilities in aqueous systems can be determined by various methods. Suitable examples are solution precipitation methods ("kinetic solubility") and methods which investigate the dissolution of a solid sample until an equilibrium is set up ("thermodynamic solubility").

a) Kinetic Solubility

A DMSO solution of the test compound (2.5 mM; 0.5 μL) is pipetted into 200 μL of an aqueous test solution (e.g. phosphate-buffered saline, 10×, 1M, Sigma, adjusted to 10 mM, pH 7.4) in a 96-well microtiter plate, and the turbidity is measured at the resulting theoretical concentration for the test compound of 6.25 μM using a nephelometer (e.g. Nephelostar Galaxy, BMG Labtech). The concentration of the test compound in the aqueous test solution is then raised to a theoretical 12.5 μM by adding further DMSO solution (2.5 mM; 0.5 μL), and the turbidity measurement is repeated. Further additions of DMSO solutions (1 μL, 2.5 mM; 0.5 μL, 10 mM; then 9×1 μL, 10 mM resulting in theoretical concentrations of 25 μM, 50 μM, 100 μM, 150 μM, 200 μM, 250 μM, 300 μM, 350 μM, 400 μM, 450 μM and 500 μM) with turbidity measurement in between complete the measurement process.

Evaluation: The turbidity values from the nephelometer are plotted against the theoretical concentration of the test compound in the aqueous test solution. As soon as a significant turbidity is detected (e.g. 5 times above the control value of the aqueous test solution) at a theoretical concentration, the level of concentration below this is stated to be the solubility limit of the test compound in the test solution. Thus, the maximum possible measurement range emerges as values <6.25 µM, 6.25-500 µM and >500 µM.

Preferred compounds of the invention show a kinetic solubility in phosphate buffer (pH 7.4) of at least 12.5 µM; more preferably of at least 50 µM and even more preferably of at least 250 µM.

b) Thermodynamic Solubility

The integrated UV absorption from HPLC UV measurement of serial dilutions of the test compound in DMSO (500 µM, 100 µM, 50 µM, 10 µM and 1 µM) shows a linear correlation with the concentration in a calibration line. The test compound (500 µg) is shaken together with the aqueous test solution (250 µL) in a closed vessel (capacity: 1.5 mL) for 16 hours (Eppendorf thermoshaker, 1400 rpm, 25° C., covering to protect from light). The sample is then centrifuged at maximum rotational speed, and the supernatant is finally filtered. A sample of the filtered supernatant is analyzed directly by HPLC UV measurement (see above). A further sample is analyzed after dilution (1 part by volume of supernatant, 39 parts by volume of test solution).

Evaluation: The concentration of the test compound in the undiluted supernatant is calculated from the resulting integrated UV absorptions of the supernatant samples on the basis of the constructed calibration lines and stated as solubility of the test compound in the respective aqueous test solution.

Examples of aqueous test solutions are deionized water or aqueous phosphate buffer with various pH values (e.g. pH 1.2; pH 4.0; pH 6.8; pH 7.4; pH 9.0) which can be prepared from the commercial solution (phosphate buffered saline, 10×, Sigma) by dilution and adjustment with phosphoric acid or sodium hydroxide solution by standard methods.

Preferred compounds of the invention show a solubility in phosphate buffer (pH 7.4) of at least 12.5 µM; more preferably of at least 50 µM and even more preferably of at least 250 µM.

Metabolic Stability

The metabolic stability is determined by incubating the test compound (5 µM) with microsomal liver fractions (1 mg/mL protein with 0.1% w/v BSA; 1 mM NADPH, 0.5% DMSO) at 37° C. Analysis at an incubation time of 0 and 20 minutes takes place by means of LCMS/MS. Further descriptions of the test system and references for the experimental procedure are to be found in Plant, N.; Drug Discovery Today 2004, 9(7), 328-336 and Lau, Y. Y. et al.; Pharmaceutical Res. 2002, 19(11), 1606-1610.

Preparation Processes

The compounds of the invention of the formula I are prepared by methods known per se in two steps.

Substituted isoxazolones can be prepared by reacting appropriately substituted acetoacetic ester derivatives IIa with hydroxylamine as described for example in Bowden K., Crank C., Ross W J., J. Chem. Soc. C 1968, 172-185. The acetoacetic ester derivatives IIa are on the one hand commercially available as marketed products or can be prepared from acetoacetic ester alkylation by methods known per se.

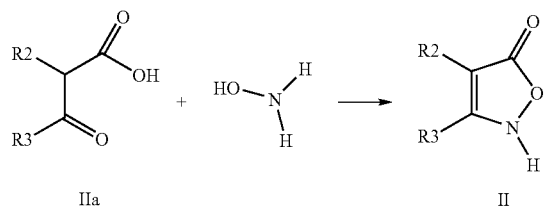

In a further step, the compounds of the invention of the formula I are prepared by acylation of the unsubstituted or substituted isoxazolones II with carbamoyl chlorides III (method A), or in two stages by reaction of 3-oxoisoxazoles II with phosgene or equivalents such as trichloromethyl chlorocarbonate, ditrichloromethyl carbonate or 4-nitrophenyl chloroformate and further reaction of the resulting isoxazolonecarboxylic acid derivative with amines IV (method B), or by reacting the isoxazolone II with the appropriate isocyanates V R1-N=C=O.

Since acids are ordinarily liberated in these reactions, it is advisable to add bases such as pyridine, triethylamine, sodium hydroxide solution or alkali metal carbonates as promoters. The reactions can be carried out in wide temperature ranges. It has ordinarily proved advantageous to operate at from 0° C. to the boiling point of the solvent used. Examples of solvents employed are methylene chloride, THF, DMF, toluene, ethyl acetate, n-heptane, dioxane, diethyl ether or pyridine. If anhydrous conditions are employed, strong bases such as lithium hydride, sodium hydride or potassium tert-butoxide in aprotic solvents such as THF or DMF have also proved useful.

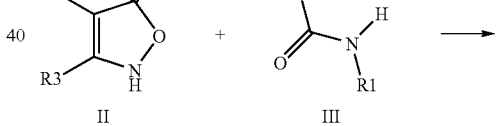

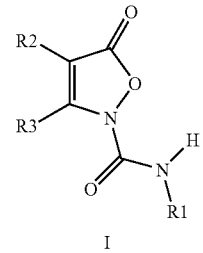

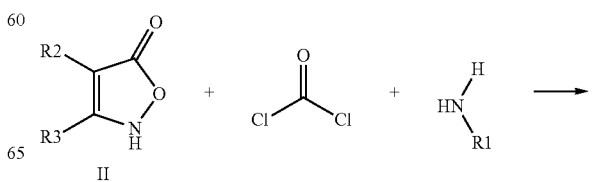

-continued

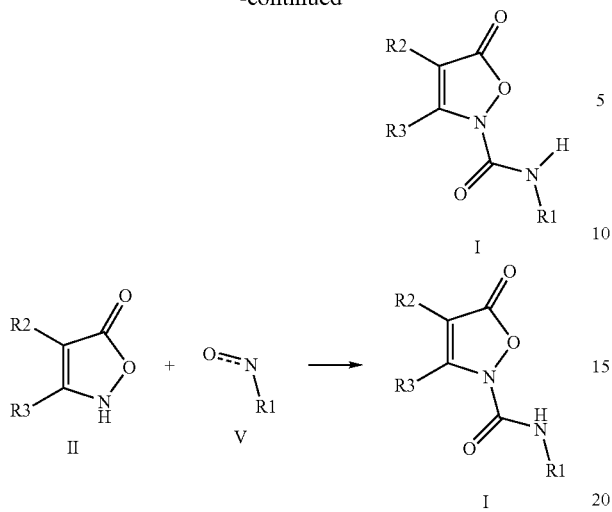

EXAMPLES

3-Cyclopropyl-2H-isoxazol-5-one

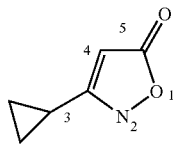

A solution of methyl 3-cyclopropyl-3-oxopropionate (4.8 g, 34 mmol) in methanol (80 mL) is mixed with hydroxylamine hydrochloride (2.6 g, 38 mmol) and triethylamine (5.3 mL, 38 mmol), and the mixture is heated under reflux for 2 h. The solvent is distilled out in vacuo. The residue is taken up in EtOAc and filtered through silica gel.

Yield: 3.2 g (75.2%).

Isoxazolones having various substituents in position 3 or having additional substituents in position 4 were prepared analogously. In these cases, either commercially available substituted acetoacetic ester derivatives were employed, or were prepared from acetoacetic ester by alkylation by methods known per se.

5-Oxo-5H-isoxazole-2-carboxamides

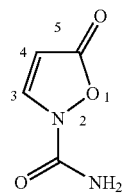

3-Cyclopropyl-5-oxo-5H-isoxazole-2-thiophene-2-ylmethylcarboxamide

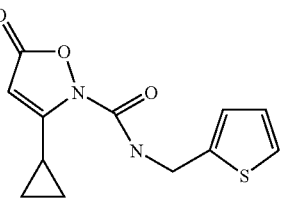

A solution of phosgene in toluene (20%, 1 mL, 2 mmol) is diluted with THF (10 mL). A solution of 3-cyclopropyl-2H-isoxazol-5-one (125 mg, 1 mmol) in THF (5 mL) is added to this solution, and triethylamine (140 μL, 1 mmol) is added to the mixture, which is stirred at 25° C. for 8 h. The precipitate is then filtered off, and the filtrate is concentrated in vacuo. The residue is taken up in THF (10 mL) and added to a solution of 2-thiophene-2-methylamine (113.2 mg, 1 mmol) in pyridine (10 mL). The mixture is stirred at 25° C. for 16 h. The solvent is then distilled out in vacuo, and the residue is purified by HPLC.

Yield: 66 mg (25%)

Correspondingly, isoxazolones with various substituents in positions 3 and 4 were converted by reaction with various amines into the corresponding 5-oxo-5H-isoxazole-2-carboxamides.

The examples detailed below serve to illustrate the invention without, however, restricting it.

| Ex. | Chemical structure | R1 |
|---|---|---|
| 1 | (4-chlorophenyl/methyl-substituted isoxazolone carboxamide structure) | 1-Ethylpropyl |

-continued
| Ex. | Chemical structure | R1 |
|---|---|---|
| 2 | 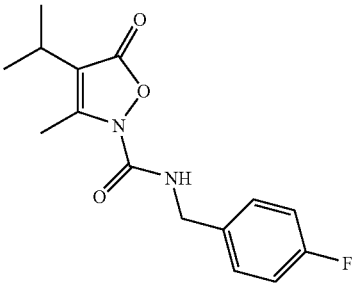 [SMILES: Cc1c(C(C)C)c(=O)on1C(=O)NCc1ccc(F)cc1] | 4-Fluorobenzyl |
| 3 | 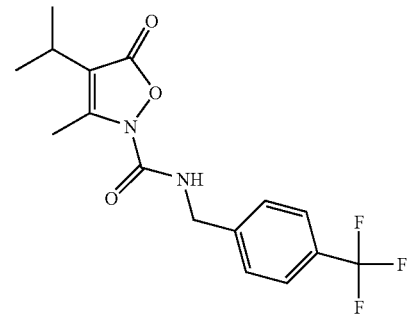 [SMILES: Cc1c(C(C)C)c(=O)on1C(=O)NCc1ccc(C(F)(F)F)cc1] | 4-Trifluoromethylbenzyl |
| 4 | 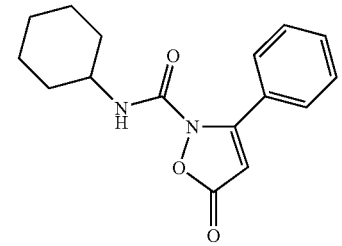 [SMILES: O=C(NC1CCCCC1)n1oc(=O)cc1-c1ccccc1] | Cyclohexyl |
| 5 | 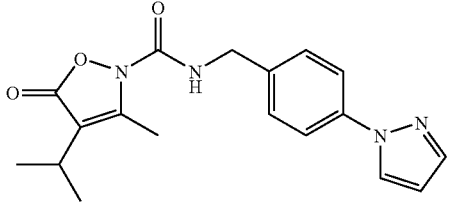 [SMILES: Cc1c(C(C)C)c(=O)on1C(=O)NCc1ccc(-n2cccn2)cc1] | 4-Pyrazol-1-ylbenzyl |
| 6 | 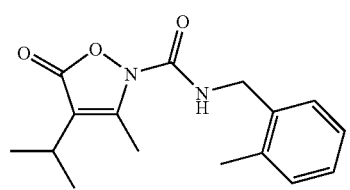 [SMILES: Cc1ccccc1CNC(=O)n1oc(=O)c(C(C)C)c1C] | 2-Methylbenzyl |
| 7 | 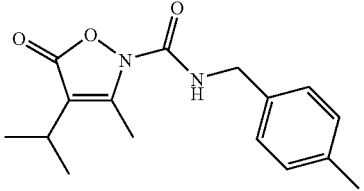 [SMILES: Cc1ccc(CNC(=O)n2oc(=O)c(C(C)C)c2C)cc1] | 4-Methylbenzyl |

-continued
| Ex. | Chemical structure | R1 |
|---|---|---|
| 8 | 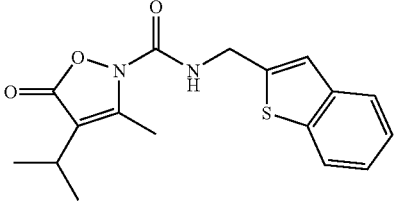 [SMILES: Cc1c(C(C)C)c(=O)on1C(=O)NCc1cc2ccccc2s1] | Benzo-[b]-thiophen-2-ylmethyl |
| 9 | 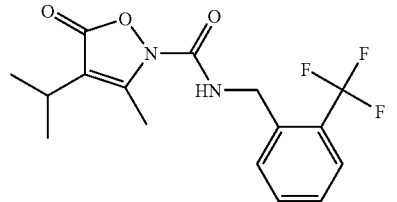 [SMILES: Cc1c(C(C)C)c(=O)on1C(=O)NCc1ccccc1C(F)(F)F] | 2-Trifluoromethyl |
| 10 | 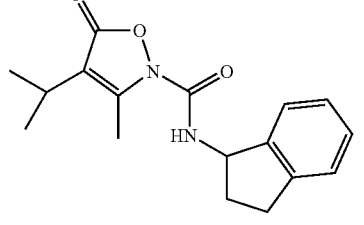 | Indan-1-yl |
| 11 | 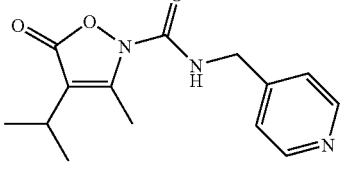 | Pyridin-4-ylmethyl |
| 12 | 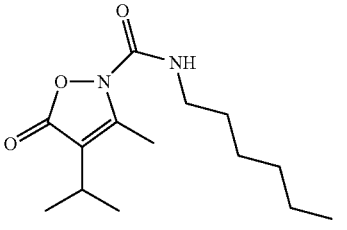 [SMILES: CCCCCCNC(=O)n1oc(=O)c(C(C)C)c1C] | n-Hexyl |
| 13 | 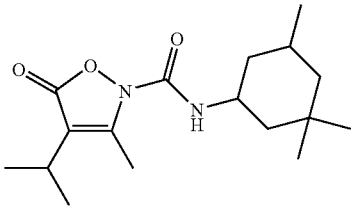 [SMILES: Cc1c(C(C)C)c(=O)on1C(=O)NC1CC(C)CC(C)(C)C1] | 3,3,5 Trimethylcyclohexyl |
| 14 | 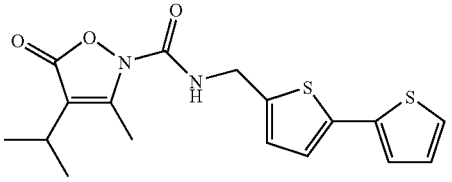 [SMILES: Cc1c(C(C)C)c(=O)on1C(=O)NCc1ccc(-c2cccs2)s1] | [2,2']Bithiophenyl-5-methyl |

-continued

| Ex. | Chemical structure | R1 |
|---|---|---|
| 15 | 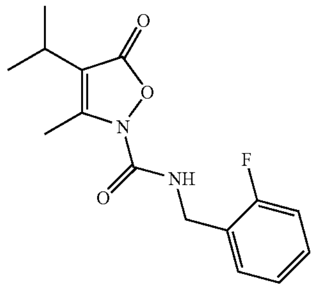 [SMILES: Cc1c(C(C)C)c(=O)on1C(=O)NCc1ccccc1F] | 2-Fluorobenzyl |
| 16 | 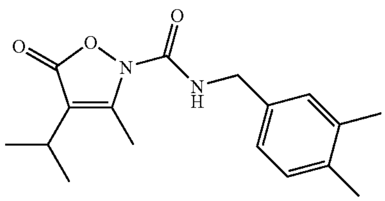 [SMILES: Cc1ccc(CNC(=O)n2oc(=O)c(C(C)C)c2C)cc1C] | 3,4-Dimethylbenzyl |
| 17 | 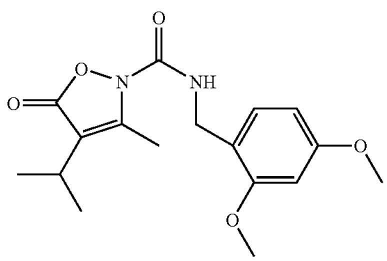 [SMILES: COc1ccc(CNC(=O)n2oc(=O)c(C(C)C)c2C)c(OC)c1] | 2,4-Dimethoxybenzyl |
| 18 | 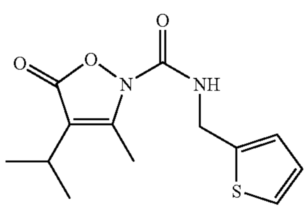 [SMILES: Cc1c(C(C)C)c(=O)on1C(=O)NCc1cccs1] | Thiophen-2-ylmethyl |
| 19 | 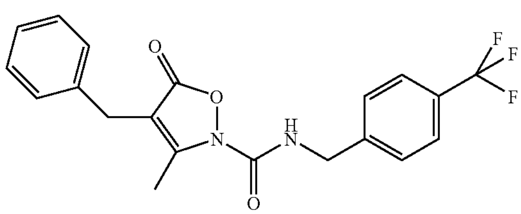 [SMILES: Cc1c(Cc2ccccc2)c(=O)on1C(=O)NCc1ccc(C(F)(F)F)cc1] | 4-Trifluoromethylbenzyl |
| 20 | 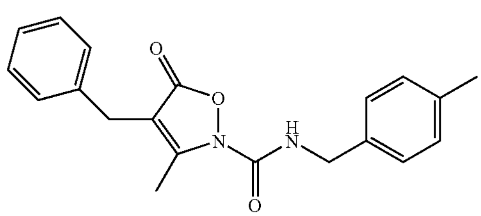 [SMILES: Cc1ccc(CNC(=O)n2oc(=O)c(Cc3ccccc3)c2C)cc1] | 4-Methylbenzyl |
| 21 | 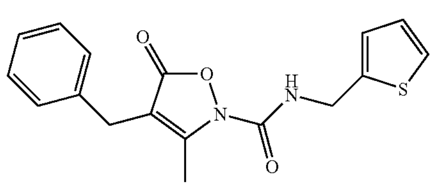 [SMILES: Cc1c(Cc2ccccc2)c(=O)on1C(=O)NCc1cccs1] | Thiophen-2-ylmethyl |

-continued

| Ex. | Chemical structure | R1 |
|---|---|---|
| 22 | 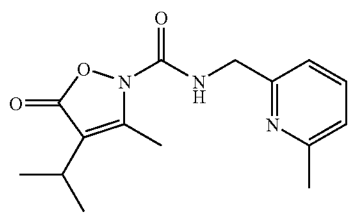 [SMILES: Cc1cccc(CNC(=O)n2oc(=O)c(C(C)C)c2C)n1] | 6-Methylpyridin-2-ylmethyl |
| 23 | 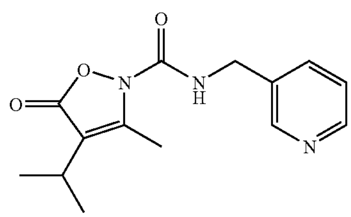 [SMILES: Cc1c(C(C)C)c(=O)on1C(=O)NCc1cccnc1] | Pyridin-3-ylmethyl |
| 24 | 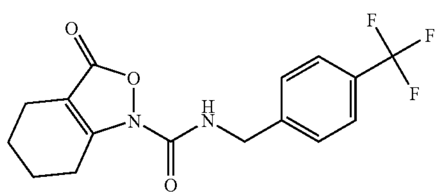 [SMILES: O=C(NCc1ccc(C(F)(F)F)cc1)n1oc(=O)c2c1CCCC2] | 4-Trifluoromethylbenzyl |
| 25 | 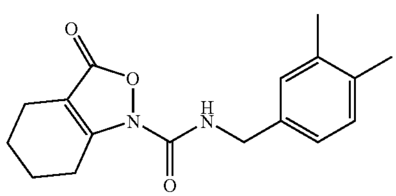 [SMILES: Cc1ccc(CNC(=O)n2oc(=O)c3c2CCCC3)cc1C] | 3,4-Dimethylbenzyl |
| 26 | 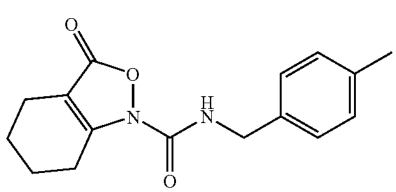 [SMILES: Cc1ccc(CNC(=O)n2oc(=O)c3c2CCCC3)cc1] | 4-Methylbenzyl |
| 27 | 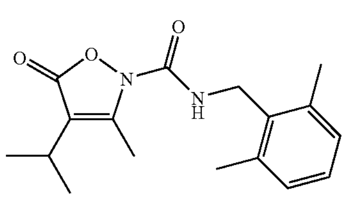 | 2,6-Dimethylbenzyl |
| 28 | 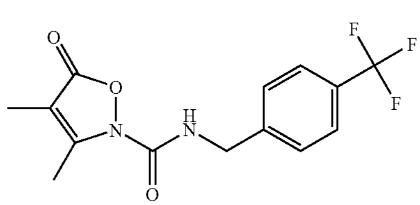 [SMILES: Cc1c(C)n(C(=O)NCc2ccc(C(F)(F)F)cc2)oc1=O] | 4-Trifluoromethylbenzyl |

-continued
| Ex. | Chemical structure | R1 |
|---|---|---|
| 29 | 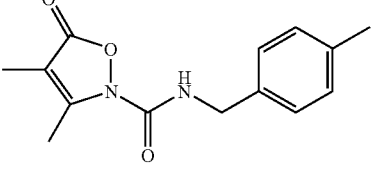 | 4-Methylbenzyl |
| 30 | 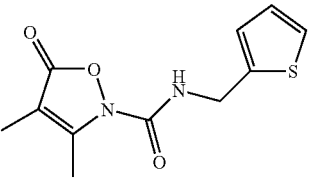 [SMILES: Cc1c(C)n(C(=O)NCc2cccs2)oc1=O] | Thiphen-2-ylmethyl |
| 31 | 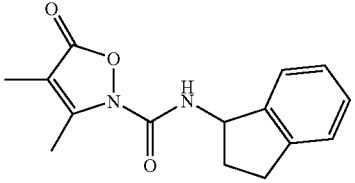 [SMILES: Cc1c(C)n(C(=O)NC2CCc3ccccc32)oc1=O] | Indan-1-yl |
| 32 | 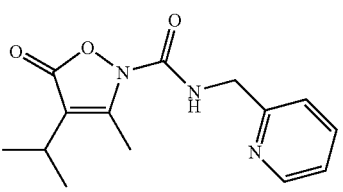 [SMILES: Cc1c(C(C)C)c(=O)on1C(=O)NCc1ccccn1] | Pyridin-2-ylmethyl |
| 33 | 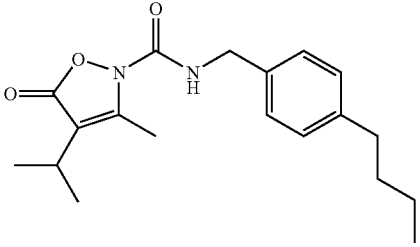 [SMILES: CCCCc1ccc(CNC(=O)n2oc(=O)c(C(C)C)c2C)cc1] | 4-Butylbenzyl |
| 34 | 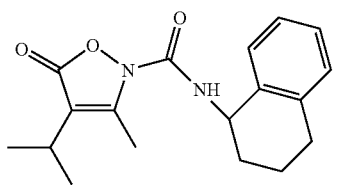 [SMILES: Cc1c(C(C)C)c(=O)on1C(=O)NC1CCCc2ccccc21] | 1,2,3,4-Tetrahydronaphthalen-1-yl |
| 35 | 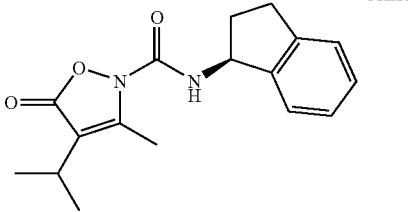 CHIRAL | (S)-Indan-1-yl |

-continued
| Ex. | Chemical structure | R1 |
|---|---|---|
| 36 | 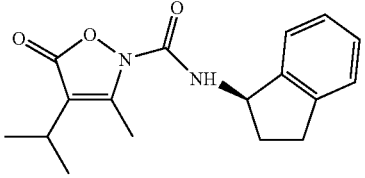 CHIRAL | (R)-Indan-1-yl |
| 37 | 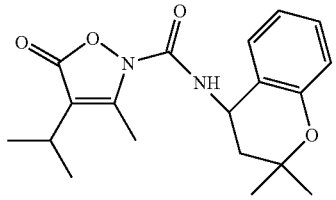 [SMILES: Cc1c(C(C)C)c(=O)on1C(=O)NC1CC(C)(C)Oc2ccccc21] | 2,2-Dimethyl-1-chroman-4-yl |
| 38 | 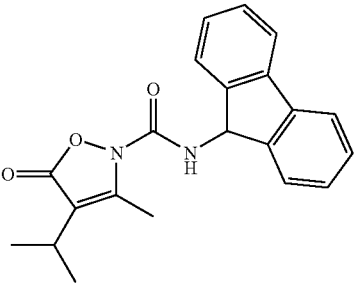 [SMILES: Cc1c(C(C)C)c(=O)on1C(=O)NC1c2ccccc2-c2ccccc21] | 9H-Fluoren-9-yl |
| 39 | 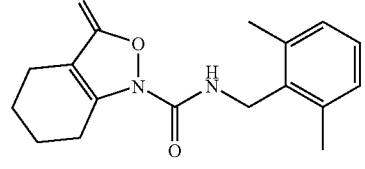 | 2,6-Dimethylbenzyl |
| 40 | 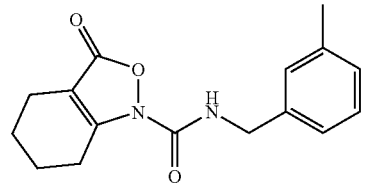 [SMILES: Cc1cccc(CNC(=O)n2oc(=O)c3c2CCCC3)c1] | 3-Methylbenzyl |
| 41 | 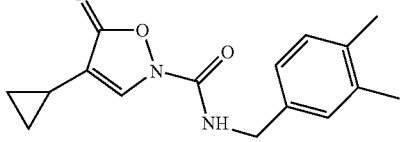 | 3,4-Dimethylbenzyl |
| 42 | 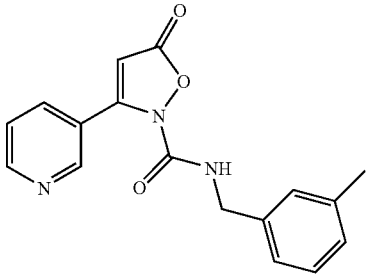 [SMILES: Cc1cccc(CNC(=O)n2oc(=O)cc2-c2cccnc2)c1] | 2-Methylbenzyl |

-continued

| Ex. | Chemical structure | R1 |
|---|---|---|
| 43 | 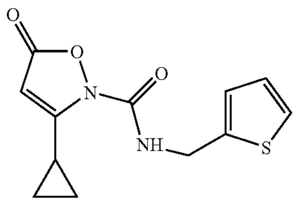 [SMILES: O=C(NCc1cccs1)n1oc(=O)cc1C1CC1] | Thiophen-2-ylmethyl |
| 44 | 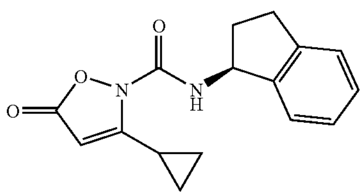 | (S)-Indan-1-yl (CHIRAL) |
| 45 | 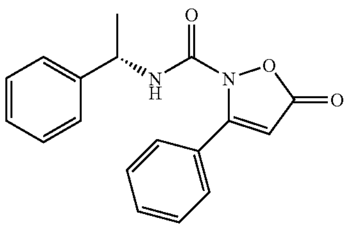 | (S)-1-Phenylethyl (CHIRAL) |
| 46 | 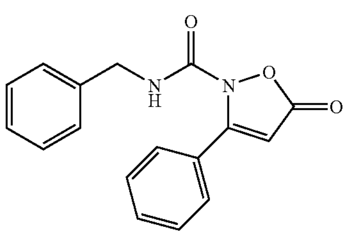 [SMILES: O=C(NCc1ccccc1)n1oc(=O)cc1-c1ccccc1] | Benzyl |
| 47 | 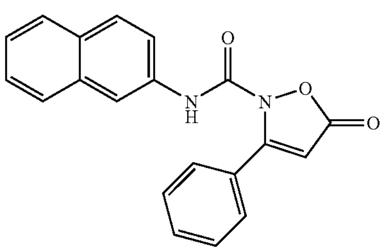 [SMILES: O=C(Nc1ccc2ccccc2c1)n1oc(=O)cc1-c1ccccc1] | 2-Naphthyl |
| 48 | 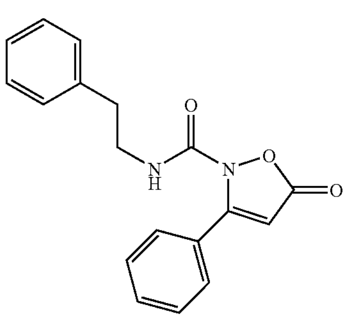 [SMILES: O=C(NCCc1ccccc1)n1oc(=O)cc1-c1ccccc1] | Phenylethyl |

-continued
| Ex. | Chemical structure | R1 |
|---|---|---|
| 49 | 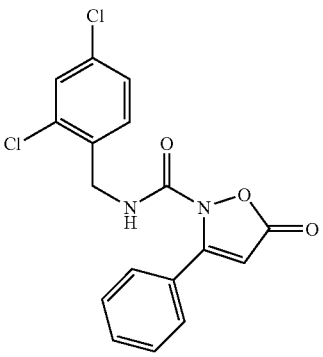 [SMILES: O=C(NCc1ccc(Cl)cc1Cl)n1oc(=O)cc1-c1ccccc1] | 3,5-Dichlorobenzyl |
| 50 | 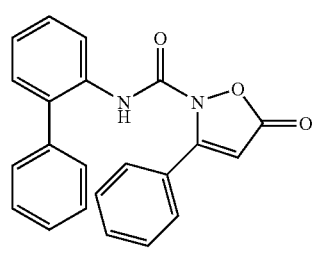 [SMILES: O=C(Nc1ccccc1-c1ccccc1)n1oc(=O)cc1-c1ccccc1] | Biphenyl-2-yl |
| 51 | 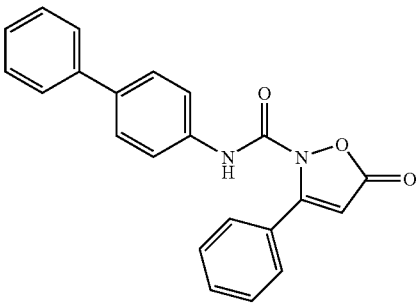 [SMILES: O=C(Nc1ccc(-c2ccccc2)cc1)n1oc(=O)cc1-c1ccccc1] | Biphenyl-4-yl |
| 52 | 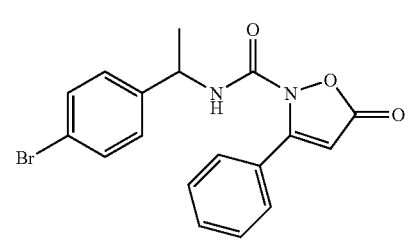 [SMILES: CC(NC(=O)n1oc(=O)cc1-c1ccccc1)c1ccc(Br)cc1] | 1-(4-bromophenyl)ethyl |
| 53 | 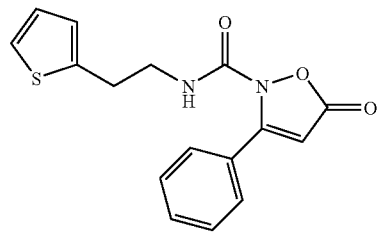 [SMILES: O=C(NCCc1cccs1)n1oc(=O)cc1-c1ccccc1] | 2-Thiophen-2-ylethyl |

-continued

| Ex. | Chemical structure | R1 |
|---|---|---|
| 54 | 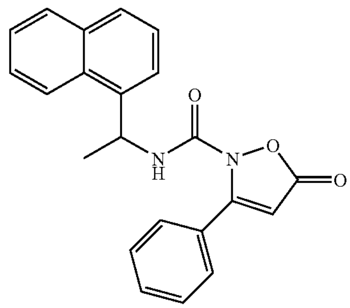 [SMILES: CC(NC(=O)n1oc(=O)cc1-c1ccccc1)c1cccc2ccccc12] | 1-Naphthalen-1ylethyl |
| 55 | 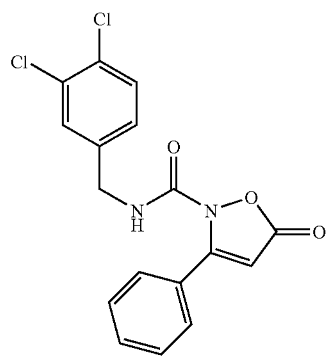 [SMILES: O=C(NCc1ccc(Cl)c(Cl)c1)n1oc(=O)cc1-c1ccccc1] | 3,4-Dichlorophenyl |
| 56 | 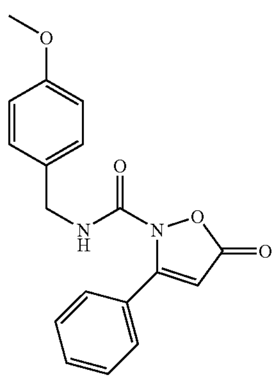 [SMILES: COc1ccc(CNC(=O)n2oc(=O)cc2-c2ccccc2)cc1] | 4-Methyloxybenzyl |
| 57 | 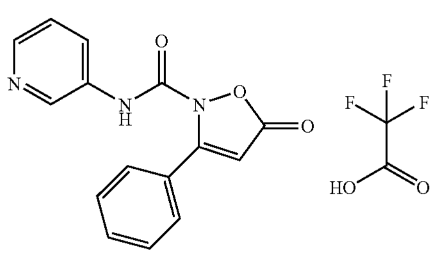 | Pyridin-3-yl |
| 58 | 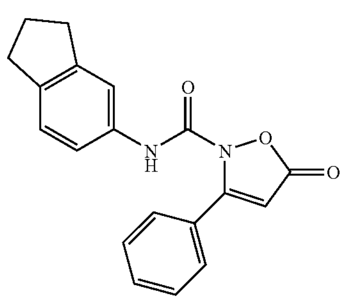 [SMILES: O=C(Nc1ccc2c(c1)CCC2)n1oc(=O)cc1-c1ccccc1] | Indan-5-yl |

| Ex. | Chemical structure | R1 |
| --- | --- | --- |
| 59 | 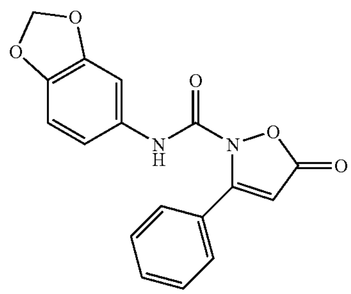 [SMILES: O=C(Nc1ccc2c(c1)OCO2)n1oc(=O)cc1-c1ccccc1] | Benzo-1,3-dioxol-5-yl |
| 60 | 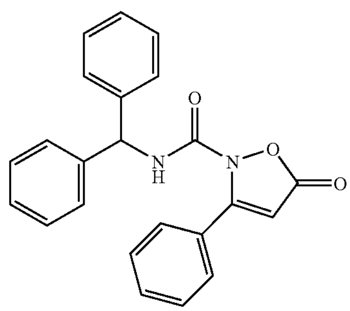 [SMILES: O=C(NC(c1ccccc1)c1ccccc1)n1oc(=O)cc1-c1ccccc1] | 1,1-Diphenylmethyl |
| 61 | 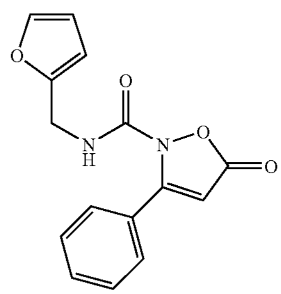 [SMILES: O=C(NCc1ccco1)n1oc(=O)cc1-c1ccccc1] | Furan-2-ylmethyl |
| 62 | 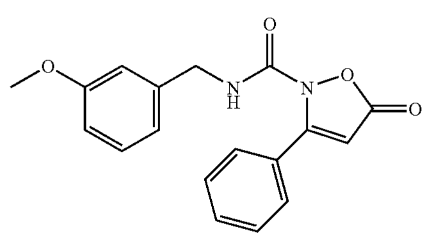 [SMILES: COc1cccc(CNC(=O)n2oc(=O)cc2-c2ccccc2)c1] | 3-Methyloxybenzyl |
| 63 | 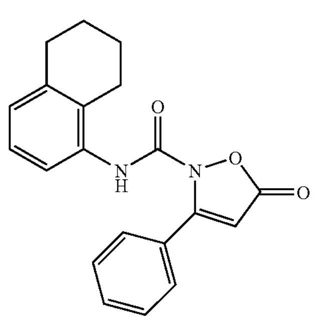 [SMILES: O=C(Nc1cccc2c1CCCC2)n1oc(=O)cc1-c1ccccc1] | 1,2,3,4-Tetrahydronaphthalen-1-yl |

-continued

| Ex. | Chemical structure | R1 |
|---|---|---|
| 64 | 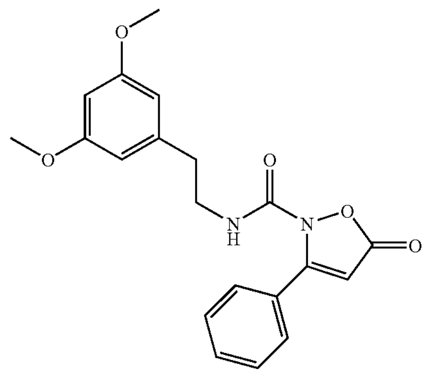 [SMILES: COc1cc(CCNC(=O)n2oc(=O)cc2-c2ccccc2)cc(OC)c1] | 2-(3,5-Dimethyloxyphenyl)ethyl |
| 65 | 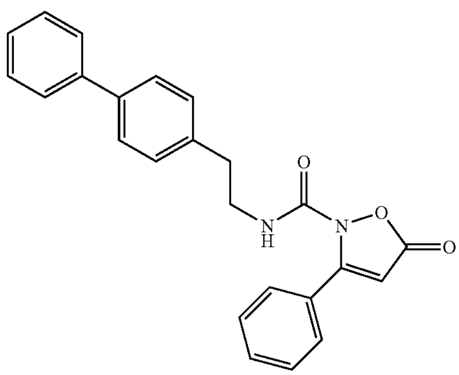 [SMILES: O=C(NCCc1ccc(-c2ccccc2)cc1)n1oc(=O)cc1-c1ccccc1] | 2-Biphenyl-4-ylethyl |
| 66 | 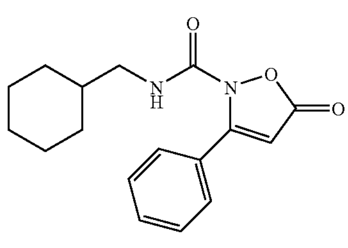 [SMILES: O=C(NCC1CCCCC1)n1oc(=O)cc1-c1ccccc1] | Cyclohexylmethyl |
| 67 | 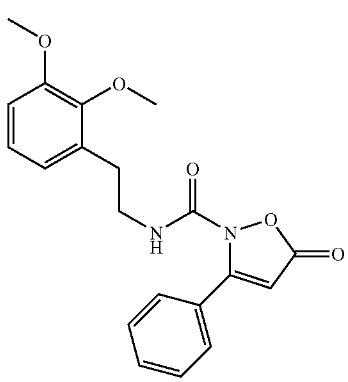 [SMILES: COc1cccc(CCNC(=O)n2oc(=O)cc2-c2ccccc2)c1OC] | 2-(2,3-Dimethyloxyphenyl)ethyl |

-continued

| Ex. | Chemical structure | | R1 |
|---|---|---|---|
| 68 | (structure) | | 2,3,4 Dichlorophenylethyl |
| 69 | (structure) | | 3,4-Dimethyloxyethylphenyl |
| 70 | (structure) | | 1,2,3,4-Tetrahydronaphthalen-1-yl |
| 71 | (structure) | CHIRAL | (R)-Indan-1-yl |

| Ex. | Chemical structure | R1 |
| --- | --- | --- |
| 72 | (structure, CHIRAL) | (S)-Indan-1-yl |
| 73 | (structure) | 2-Methylbenzyl |
| 74 | (structure) | 2-Methylbenzyl |
| 75 | (structure) | 3,4-Dimethylbenzyl |
| 76 | (structure) | Thiophen-2-ylmethyl |
| 77 | (structure) | Thiophen-2-ylmethyl |

-continued

| Ex. | Chemical structure | | R1 |
|---|---|---|---|
| 78 | 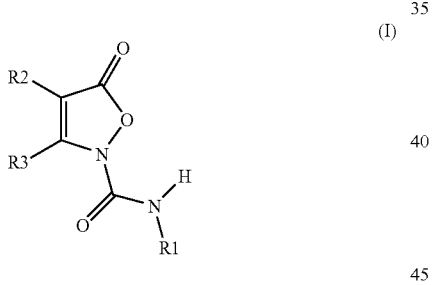 | CHIRAL | (S)-Indan-1-yl |
| 79 | 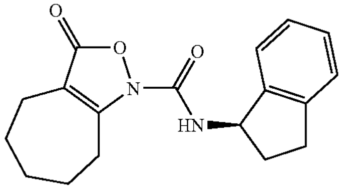 | CHIRAL | (R)-Indan-1-yl |
| 80 | 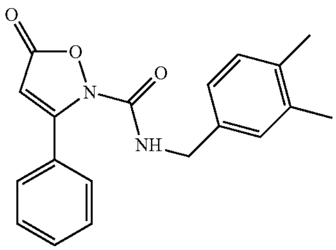 [SMILES: Cc1ccc(CNC(=O)n2oc(=O)cc2-c2ccccc2)cc1C] | | 3,4-Dimethylbenzyl |

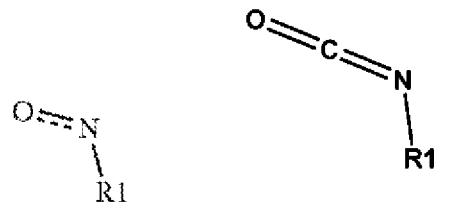

The invention claimed is:

1. A compound of the formula I

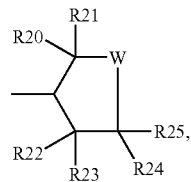

wherein:

R1 is selected from $(C_5-C_{16})$-alkyl, Y-aryl, and Y-heteroaryl, wherein aryl is substituted one or more times by groups selected from OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $CH_2CH_3$, —$CH_2$—$CH_2$—$CH_2$—$CH_3$, $(C_2-C_4)$-haloalkyl, O—$(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, $(C_0-C_8)$-alkylene-aryl, O—$(C_0-C_8)$-alkylene-aryl, S-aryl, $(C_0-C_8)$-alkylene-heteroaryl, N(R4)(R5), $SO_2$—$CH_3$, $SO_2$—$NH_2$, $SF_5$, COOH, COO—$(C_1-C_6)$-alkyl, CON(R6)(R7), N(R8)CO(R9), N(R10)$SO_2$(R11), CO(R12), $(CR13R14)_x$—O(R15), O—CO—N(R16)(R17), O—CO—$(C_1-C_6)$-alkylene-CO—O—$(C_1-C_6)$-alkyl, O—CO—$(C_1-C_6)$-alkylene-CO—OH, and O—CO—$(C_1-C_6)$-alkylene-CO—N(R18)(R19), wherein heteroaryl in Y-heteroaryl is optionally substituted one or more times by the aforesaid groups, wherein aryl or heteroaryl in the aforesaid groups is optionally substituted one or more times by groups selected from F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, $(C_2-C_6)$-alkenyl, $(C_3-C_8)$-cycloalkyl, O—$(C_3-C_8)$-cycloalkyl, $(C_2-C_6)$-alkynyl, N(R4a)(R5a), $SO_2$—$CH_3$, $SF_5$, COOH, COO—$(C_1-C_6)$-alkyl, CON(R6a)(R7a), N(R8a)CO(R9a), N(R10a)$SO_2$(R11a), CO(R12a), $(CR13aR14a)_{x'-O(R}15a)$, O—CO—N(R16a)(R17a), O—CO—$(C_1-C_6)$-alkylene-CO—O—$(C_1-C_6)$-alkyl, O—CO—$(C_1-C_6)$-alkylene-CO—OH, and O—CO—$(C_1-C_6)$-alkylene-CO—N(R18a)(R19a);

x, x' are selected from 0, 1, 2, 3, 4, 5, and 6;

R4, R5, R6, R7, R9, R10, R11, R12, R13, R14, R15, R16, R17, R18, R19, R4a, R5a, R6a, R7a, R9a, R10a, R11a, R12a, R13a, R14a, R15a, R16a, R17a, R18a, and R19a are independently selected from hydrogen, $(C_1-C_8)$-alkyl, and a radical of the formula Ia wherein W is selected from —C(R26)(R27)-, —C(R26)(R27)-C(R28)(R29)-, and —C(R26)(R27)-O; R20, R21, R22, R23, R24, R25, R26, R27, R28, R29 are independently selected from F, Cl, Br, I, OH, $CF_3$, $NO_2$, CN, $OCF_3$, $SF_5$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_4)$-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, N(R30)(R31), $SO_2$—$CH_3$, COOH, COO—($C_1$-$C_6$)-alkyl, CON(R32)(R33), N(R34)CO(R35), N(R36)$SO_2$(R37), CO(R38), (CR39R40)$_{x''}$, —O(R41), O—CO—N(R42)(R43), O—CO—($C_1$-$C_6$)-alkylene-CO—O—($C_1$-$C_6$)-alkyl, O—CO—($C_1$-$C_6$)-alkylene-CO—OH, and O—CO—($C_1$-$C_6$)-alkylene-CO—N(R44)(R45);

x" is selected from 0, 1, 2, 3, 4, 5, and 6;

R30, R31, R32, R33, R34, R35, R36, R37, R38, R39, R40, R41, R42, R43, R44, and R45 are independently selected from hydrogen and ($C_1$-$C_6$)-alkyl;

or

R20 and R26, or R21 and R27, together with the carbon atoms carrying them, form a monocyclic, 5- or 6-membered saturated, partly unsaturated, or aromatic ring system whose individual members may be replaced by —CHR46-, —CR46R47-, or =(C—R46)-;

or

R22 and R24, or R23 and R25, together with the carbon atoms carrying them, form a monocyclic, 5- or 6-membered saturated, partly unsaturated, or an aromatic ring system whose individual members may be replaced by —CHR46-, —CR46R47-, or =(C—R46)-;

R46 and R47 are independently selected from F, Cl, Br, I, OH, $CF_3$, $NO_2$, CN, $OCF_3$, $SF_5$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_2$-$C_6$)-alkynyl, N(R48)(R49), $SO_2$—$CH_3$, COOH, COO—($C_1$-$C_6$)-alkyl, CON(R50)(R51), N(R52)CO(R53), N(R54)$SO_2$(R55), CO(R56), (CR57R58)$_{x'''}$, —O(R59), O—CO—N(R60)(R61), O—CO—($C_1$-$C_6$)-alkylene-CO—O—($C_1$-$C_6$)-alkyl, O—CO—($C_1$-$C_6$)-alkylene-CO—OH, and O—CO—($C_1$-$C_6$)-alylene-CO—N(R62)(R63);

x''' is selected from 0, 1, 2, 3, 4, 5, and 6;

R48, R49, R50, R51, R52, R53, R54, R55, R56, R57, R58, R59, R60, R61, R62, and R63 are independently selected from hydrogen and ($C_1$-$C_6$)-alkyl;

Y and Z are independently selected from ($C_1$-$C_2$)-alkylene, which is optionally substituted once by F, Cl, $CH_3$ or OH;

R2 is selected from hydrogen, ($C_1$-$C_{12}$)-alkyl and Z-aryl, wherein aryl is optionally substituted by ($C_3$-$C_{12}$)-cycloalkyl;

R3 is selected from ($C_1$-$C_{12}$)-alkyl, aryl, and heteroaryl, wherein aryl or heteroaryl is optionally substituted by ($C_3$-$C_{12}$)-cycloalkyl; or R2 and R3, together with the carbon atoms carrying them, form a monocyclic, saturated, or partly unsaturated 4- to 8-membered ring system whose individual members may be replaced by one to three atoms or atomic groups selected from —CHR64-, —CR64R65-, =(C—R66)-, —NR67-, —C(=O)—, and —O—, with the proviso that two units from the series —O— may not be adjacent;

R64, R65, R66, and R67 are independently selected from hydrogen, F, Cl, Br, I, OH, $CF_3$, $NO_2$, CN, $OCF_3$, $SF_5$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_4$)-haloalkyl, O—($C_2$-$C_4$)-haloalkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, N(R68)(R69), $SO_2$—$CH_3$, COOH, COO—($C_1$-$C_6$)-alkyl, CON(R70)(R71), N(R72)CO(R73), N(R74)$SO_2$(R75), CO(R76), (CR77R78)$_{x''''}$—O(R79), O—CO—N(R80)(R81), O—CO—($C_1$-$C_6$)-alkylene-CO—O—($C_1$-$C_6$)-alkyl, O—CO—($C_1$-$C_6$)-alkylene-CO—OH, and O—CO—($C_1$-$C_6$)-alkylene-CO—N(R82)(R83);

x"" is selected from 0, 1, 2, 3, 4, 5, and 6;

R68, R69, R70, R71, R72, R73, R74, R75, R76, R77, R78, R79, R80, R81, R82, and R83 are independently selected from hydrogen and ($C_1$-$C_6$)-alkyl;

with the proviso that the compound with R1=cyclohexyl, R2=H, and R3=phenyl is excluded;

including tautomeric forms of the compound and their physiologically tolerated salts.

2. A compound according to claim 1, wherein

R1 is selected from ($C_5$-$C_{12}$)-alkyl, Y-phenyl, and Y-heteroaryl, wherein heteroaryl includes one heteroatom selected from N, O, and S, and wherein phenyl is substituted one or more times by groups selected from OH, $CF_3$, $NO_2$, CN, $OCF_3$, O—($C_1$-$C_6$)-alkyl, S—($C_1$-$C_6$)-alkyl, $CH_2CH_3$, —$CH_2$—$CH_2$—$CH_2$—$CH_3$, ($C_2$-$C_4$)-haloalkyl, ($C_3$-$C_8$)-cycloalkyl, ($C_0$-$C_6$)-alkylene-phenyl, O—($C_0$-$C_6$)-alkylene-phenyl, S-phenyl, ($C_0$-$C_8$)-alkylene-heteroaryl, N(R4)(R5), COOH, COO—($C_1$-$C_6$)-alkyl, CON(R6)(R7), and CO(R12), wherein heteroaryl in Y-heteroaryl is optionally substituted one or more times by the aforesaid groups, wherein phenyl or heteroaryl in the aforesaid groups is optionally substituted one or more times by groups selected from F, Cl, OH, $CF_3$, $NO_2$, CN, $OCF_3$, O—($C_1$-$C_6$)-alkyl, S—($C_1$-$C_6$)-alkyl, ($C_1$-$C_6$)-alkyl, ($C_2$-$C_4$)-haloalkyl, ($C_3$-$C_8$)-cycloalkyl, N(R4a)(R5a), COOH, COO—($C_1$-$C_6$)-alkyl, and CON(R6a)(R7a) CO(R12a);

x, x' are selected from 0, 1, 2, 3, 4, 5, and 6;

R4, R5, R6, R7, R12, R4a, R5a, R6a, R7a, and R12a are independently selected from hydrogen, ($C_1$-$C_8$)-alkyl, and a radical of the formula Ib

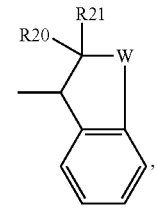

wherein W is selected from —C(R26)(R27)-, —C(R26)(R27)-C(R28)(R29)-, and —C(R26)(R27)-O—;

R20, R21, R26, R27, R28, and R29 are independently selected from hydrogen, F, Cl, OH, $CF_3$, $NO_2$, CN, $OCF_3$, O—($C_1$-$C_6$)-alkyl, ($C_1$-$C_6$)-alkyl, and CO—($C_1$-$C_6$)-alkyl;

or

R20, R21, R26 and R27, together with the carbon atoms carrying them, form a fused benzene residue, which is optionally substituted one or more times by groups selected from F, Cl, CN, $NO_2$, $CF_3$, $OCF_3$, ($C_1$-$C_6$)-alkyl, O—($C_1$-$C_6$)-alkyl, and CO—($C_1$-$C_6$)-alkyl;

Y and Z are independently selected from —$CH_2$— and —$CH_2$—$CH_2$—, which are optionally substituted once by $CH_3$ or OH;

R2 is selected from hydrogen, ($C_1$-$C_{12}$)-alkyl, and Z-phenyl, wherein phenyl is optionally substituted by ($C_3$-$C_{12}$)-cycloalkyl;

R3 is selected from ($C_1$-$C_{12}$)-alkyl, phenyl, and heteroaryl, wherein heteroaryl includes one heteroatom selected from N, O, and S, wherein phenyl or heteroaryl is optionally substituted by $(C_3-C_{12})$-cycloalkyl; or R2 and R3, together with the carbon atoms carrying them, form a monocyclic, saturated 5- to 7-membered ring system whose individual members may be replaced by one to three atomic groups selected from —CHR64-, —CR64R65-, and =(C—R66)-;

R64, R65, and R66 are independently selected from F, Cl, OH, $CF_3$, O—$(C_1-C_4)$-alkoxy-$(C_1-C_4)$-alkyl, $(C_1-C_6)$-alkyl, $(C_2-C_4)$-haloalkyl, $(C_3-C_8)$-cycloalkyl, N(R68)(R69), $SO_2$—$CH_3$, COOH, COO—$(C_1-C_6)$-alkyl, CON(R70)(R71), N(R72)CO(R73), CO(R76), O—CO—N(R80)(R81), O—CO—$(C_1-C_6)$-alkylene-CO—O—$(C_1-C_6)$-alkyl, O—CO—$(C_1-C_6)$-alkylene-CO—OH, and O—CO—$(C_1-C_6)$-alkylene-CO—N(R82)(R83);

R68, R69, R70, R71, R72, R73, R76, R77, R78, R79, R80, R81, R82, and R83 are independently selected from hydrogen and $(C_1-C_6)$-alkyl;

including tautomeric forms of the compound, and their physiologically tolerated salts.

3. A compound according to claim 2, wherein

R1 is selected from $(C_5-C_8)$-alkyl, Y-phenyl, Y-pyridyl, Y-thienyl, Y-furyl, Y-benzothienyl, and Y-benzofuryl, wherein phenyl in Y-phenyl is substituted once, twice, or three times by groups selected from $CF_3$, CN, $OCF_3$, O—$(C_1-C_6)$-alkyl, $CH_2CH_3$, —$CH_2$—$CH_2$—$CH_2$—$CH_3$, $(C_3-C_6)$-cycloalkyl, N(R4)(R5), COOH, COO—$(C_1-C_6)$-alkyl, CON(R6)(R7), and CO(R12), and is optionally substituted once by groups selected from $(C_0-C_1)$-alkylene-phenyl, O—$(C_0-C_1)$-phenyl, pyrazolyl, pyridyl, thienyl, furyl, benzothienyl, and benzofuryl, wherein Y-pyridyl, Y-thienyl, Y-furyl, or Y-benzothienyl is optionally substituted one or more times by the aforesaid groups, wherein a heteroaromatic radical or phenyl of the aforesaid groups is optionally substituted once, twice, or three times by groups selected from F, Cl, Br, $CF_3$, CN, $OCF_3$, O—$(C_1-C_6)$-alkyl, $(C_1-C_6)$-alkyl, $(C_3-C_6)$-cycloalkyl, N(R4a)(R5a), COOH, COO—$(C_1-C_6)$-alkyl, CON(R6a)(R7a), and CO(R12a);

R4, R5, R6, R7, R12, R4a, R5a, R6a, R7a, and R12a are independently selected from H, $(C_1-C_8)$-alkyl, and a radical selected from the group

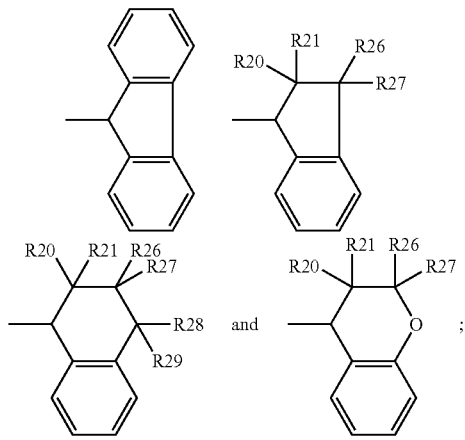

R20, R21, R26, R27, R28, R29 are independently selected from hydrogen and $(C_1-C_6)$-alkyl;

Y is selected from —$CH_2$— and —$CH_2$—$CH_2$—, which are optionally substituted once by $CH_3$;

R2 is selected from hydrogen, $(C_1-C_8)$-alkyl, and —$CH_2$-phenyl, wherein phenyl is optionally substituted by $(C_3-C_8)$-cycloalkyl;

R3 is selected from $(C_1-C_8)$-alkyl, phenyl, pyridyl, and thienyl, wherein phenyl, pyridyl, or thienyl is optionally substituted by $(C_3-C_8)$-cycloalkyl; or R2 and R3, together with the carbon atoms carrying them, form a monocyclic, saturated 6- to 7-membered ring system whose individual members may be replaced by one to three atoms or atomic groups selected from —CHR64- and —CR64R65-;

R64 and R65 are independently selected from F, Cl, $CF_3$, $OCF_3$, $(C_1-C_6)$-alkyl, O—$(C_1-C_6)$-alkyl, N(R68)(R69), COOH, COO—$(C_1-C_6)$-alkyl, CO—N(R70)(R71), and CO(R76);

R68, R69, R70, R71, and R76 are independently selected from hydrogen and $(C_1-C_6)$-alkyl;

including tautomeric forms of the compound, and their physiologically tolerated salts.

4. A compound of the formula I as claimed in claim 3, wherein

R2 is isopropyl and

R3 is methyl.

5. A compound of the formula I as claimed in claims 1 to 3, wherein

R2 is hydrogen and

R3 is phenyl, which is optionally substituted once by Cl.

6. A compound of the formula I as claimed in claims 1 to 3, wherein

R2 and R3 together are —$CH_2$—$CH_2$—$CH_2$—$CH_2$— or —$CH_2$—$CH_2$—$CH_2$—$CH_2$—$CH_2$—.

7. A compound according to claim 3, wherein

R1 is selected from $(C_5-C_7)$-alkyl, Y-phenyl, Y-thienyl, and Y-benzothienyl, wherein phenyl in Y-phenyl is substituted once, twice, or three times by groups selected from $CF_3$, O—$CH_3$, —$CH_2CH_3$, and —$CH_2$—$CH_2$—$CH_2$—$CH_3$, and is optionally substituted once by phenyl, pyrazolyl or thienyl, wherein phenyl, pyrazolyl, or thienyl is optionally substituted once, twice or three times by F, Cl, Br, $CF_3$, O—$(C_1-C_6)$-alkyl, $(C_1-C_6)$-alkyl;

or R1 is selected from the following groups:

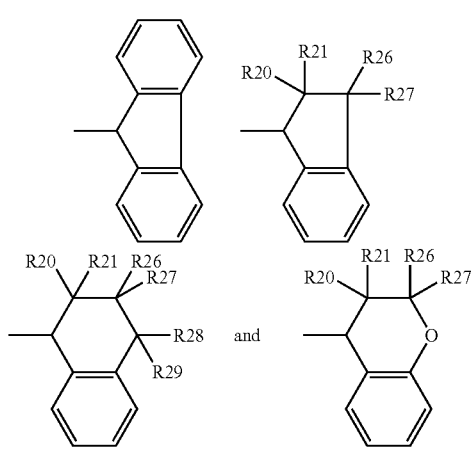

wherein R20, R21, R26, R27, R28, and R29 are independently selected from hydrogen and $CH_3$;

Y is —$CH_2$—, which is optionally substituted once by $CH_3$;

R2 is selected from hydrogen, methyl, isopropyl, cyclopropyl, phenyl, and —CH$_2$-phenyl, wherein phenyl is optionally substituted by Cl in position 4;

R3 is selected from methyl, phenyl, pyridyl, and cyclopropyl, wherein phenyl may be is optionally substituted by Cl; or R2 and R3 are together —CH$_2$—CH$_2$—CH$_2$—CH$_2$— or —CH$_2$—CH$_2$—CH$_2$—CH$_2$—CH$_2$—.

8. A medicament comprising one or more compounds of the formula I as claimed in claim 1.

9. A process for the manufacture of a medicament comprising one or more of the compounds of the formula I as claimed in claim 1, which comprises mixing the latter with a pharmaceutically suitable carrier, and converting this mixture into a form suitable for administration.

10. A process for preparing compounds of the formula I as claimed in claim 1, which comprises 3-oxoisoxazole derivatives of the formula II a) being acylated with carbamoyl chlorides of the formula III;

or b) in two stages being reacted first with phosgene or equivalents such as trichloromethyl chlorocarbonate, ditrichloromethyl carbonate or 4-nitrophenyl chloroformate and in a second step with amines of the formula IV, or c) being reacted with isocyanates of the formula V:
O═C═N—R1, in which the substituents have the abovementioned meanings

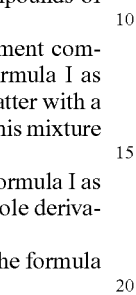
II

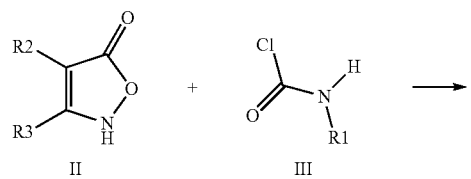
II          III

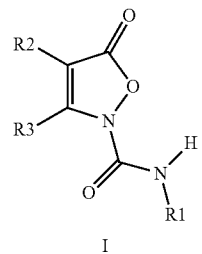
I

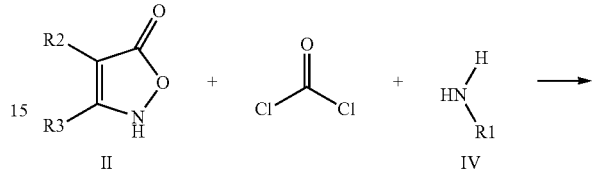
II          IV

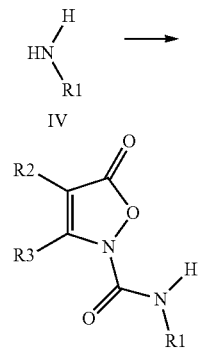
I

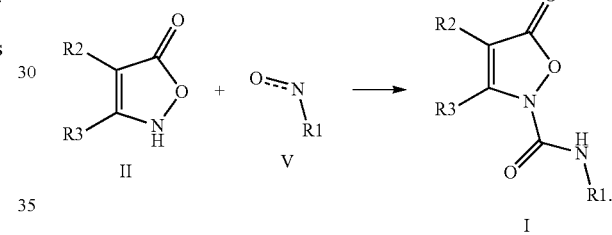
II          V

I

* * * * *

UNITED STATES PATENT AND TRADEMARK OFFICE
CERTIFICATE OF CORRECTION

PATENT NO. : 9,029,400 B2
APPLICATION NO. : 12/573335
DATED : May 12, 2015
INVENTOR(S) : Stefan Petry et al.

Page 1 of 2

It is certified that error appears in the above-identified patent and that said Letters Patent is hereby corrected as shown below:

In the Specification:

At column 37, starting on line 15, formula V, please replace:

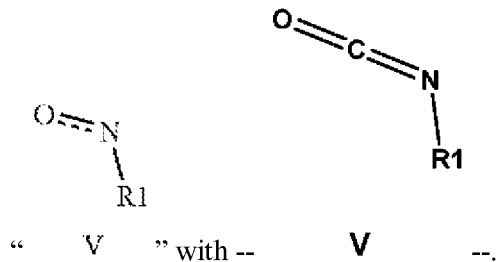

" V " with -- V --.

In the Claims:

At column 66, claim number 1, line number 40, please replace:

"$(CR13aR14a)_x\text{-}O(R15a)$," with --$(CR13aR14a)_x\text{-}O(R15a)$,--;

At column 67, claim number 1, line number 6, please replace:

"$(CR39R40)_{x''}\text{-}O(R41)$," with --$(CR39R40)_{x''}\text{-}O(R41)$,--;

At column 67, claim number 1, line number 34, please replace:

"$(CR57R58)_{x'''}\text{-}O(R59)$," with --$(CR57R58)_{x'''}\text{-}O(R59)$,--;

At column 68, claim number 2, line number 32, please replace:

"CON(R6a)(R7a)" with --CON(R6a)(R7a),--;

Signed and Sealed this
Twenty-ninth Day of March, 2016

Michelle K. Lee
*Director of the United States Patent and Trademark Office*

At column 69, claim number 2, line number 9, please replace:

"$CF_3$, O-($C_1$-$C_4$)-alkoxy-($C_1$-$C_4$)-alkyl," with

--$CF_3$, O-($C_1$-$C_6$)-alkyl, O-($C_1$-$C_4$)-alkoxy-($C_1$-$C_4$)-alkyl,--;

At column 69, claim number 3, line number 30, please replace:

"O-($C_0$-$C_1$)-phenyl," with --O-($C_0$-$C_1$)-alkylene-phenyl,--;

At column 71, claim number 7, line number 5, please delete "may be"; and

At column 72, claim number 10, starting on line 30, formula V, please replace: